(12) United States Patent
Fairbank, Jr. et al.

(10) Patent No.: US 11,878,297 B2
(45) Date of Patent: Jan. 23, 2024

(54) FLUID SPECIMEN TESTING

(71) Applicant: ABBOTT TOXICOLOGY LIMITED, Abingdon (GB)

(72) Inventors: Nigel John Fairbank, Jr., Abingdon (GB); Barry Lillis, Abingdon (GB); Timothy John Abbott, Abingdon (GB); Paul Ngui, Abingdon (GB)

(73) Assignee: ABBOTT TOXICOLOGY LIMITED, Abingdon (GB)

( * ) Notice: Subject to any disclaimer, the term of this patent is extended or adjusted under 35 U.S.C. 154(b) by 0 days.

(21) Appl. No.: 16/892,114

(22) Filed: Jun. 3, 2020

(65) Prior Publication Data

US 2020/0384460 A1 Dec. 10, 2020

Related U.S. Application Data

(60) Provisional application No. 62/857,073, filed on Jun. 4, 2019.

(51) Int. Cl.
*B01L 3/00* (2006.01)
*G01N 33/94* (2006.01)

(52) U.S. Cl.
CPC ............ *B01L 3/502* (2013.01); *B01L 3/5457* (2013.01); *G01N 33/94* (2013.01);
(Continued)

(58) Field of Classification Search
CPC .... B01L 3/502; B01L 3/5457; B01L 2200/02; B01L 2200/0605; B01L 2200/141; B01L 2300/021; B01L 2300/048; B01L 2200/0684; B01L 2300/023; B01L 2300/0672; B01L 2300/069; B01L 2300/0825; B01L 2300/0832; B01L 2300/087; B01L 2400/0406; B01L 2400/0694; B01L 3/5023; G01N 33/94; A61B 5/14507; A61B 5/207; A61B 5/4845
(Continued)

(56) References Cited

U.S. PATENT DOCUMENTS 4,094,647 A 6/1978 Deutsch et al.
4,235,601 A 11/1980 Deutsch et al.
(Continued)

FOREIGN PATENT DOCUMENTS

EP 0284232 9/1988
EP 0505636 9/1992
(Continued)

OTHER PUBLICATIONS

Bangs Laboratories TechNote 303 "Lateral Flow Tests" (Mar. 20, 2013).
(Continued)

*Primary Examiner* — Benjamin R Whatley
*Assistant Examiner* — Jacqueline Brazin
(74) *Attorney, Agent, or Firm* — Casimir Jones, S.C.; Thomas A. Isenbarger

(57) ABSTRACT

Provided herein is technology relating to testing fluid specimens and particularly, but not exclusively, to apparatuses, devices, methods, systems, and kits for testing a fluid specimen, e.g. urine, saliva, or other body fluids, to detect specified chemical components in the specimen.

12 Claims, 22 Drawing Sheets

(52) U.S. Cl.
CPC ... *B01L 2200/02* (2013.01); *B01L 2200/0605* (2013.01); *B01L 2200/141* (2013.01); *B01L 2300/021* (2013.01); *B01L 2300/048* (2013.01)

(58) Field of Classification Search
USPC ......................................................... 422/63
See application file for complete search history.

(56) References Cited

U.S. PATENT DOCUMENTS

| | | | |
|---|---|---|---|
| 4,275,149 | A | 6/1981 | Litman et al. |
| 4,299,916 | A | 11/1981 | Litman et al. |
| 4,361,537 | A | 11/1982 | Deutsch et al. |
| 4,366,241 | A | 12/1982 | Tom et al. |
| 5,120,643 | A | 6/1992 | Ching et al. |
| 5,141,850 | A | 8/1992 | Cole et al. |
| 5,160,701 | A | 11/1992 | Brown et al. |
| 5,415,994 | A | 5/1995 | Imrich et al. |
| 5,451,504 | A | 9/1995 | Fitzpatrick et al. |
| 5,559,041 | A | 9/1996 | Kang et al. |
| 5,569,608 | A | 10/1996 | Sommer et al. |
| 5,591,401 | A * | 1/1997 | Sayles ..................... B01L 3/502 422/417 |
| 5,622,871 | A | 4/1997 | May et al. |
| 5,798,273 | A | 8/1998 | Shuler et al. |
| 5,837,546 | A | 11/1998 | Allen et al. |
| 6,342,183 | B1 | 1/2002 | Lappe et al. |
| 6,352,862 | B1 | 3/2002 | Davis et al. |
| 6,841,159 | B2 | 1/2005 | Simonson |
| 7,344,893 | B2 | 3/2008 | Kirkegaard et al. |
| 7,537,733 | B2 * | 5/2009 | Lappe .............. G01N 33/54366 422/82.05 |
| 2002/0046614 | A1 * | 4/2002 | Alley ..................... B01L 3/502 73/864.51 |
| 2003/0186446 | A1 * | 10/2003 | Pugh ................ G01N 33/48778 436/46 |
| 2005/0074362 | A1 | 4/2005 | Lappe et al. |
| 2009/0029341 | A1 * | 1/2009 | Fuhr ....................... A01N 1/00 435/1.3 |
| 2016/0252503 | A1 | 9/2016 | Jian-Feng |
| 2019/0232279 | A1 * | 8/2019 | Jensen .............. B01L 3/502707 |

FOREIGN PATENT DOCUMENTS

| | | |
|---|---|---|
| WO | WO 1988/08534 | 11/1988 |
| WO | WO 1991/12336 | 8/1991 |
| WO | WO 2014/013213 | 1/2014 |

OTHER PUBLICATIONS

Davidson, C. et al., Spicing Up Pharmacology: A Review of Synthetic Cannabinoids From Structure to Adverse Events. Adv Pharmacol. 2017;80:135-168.

Ford, B.M. et al., Synthetic Pot: Not Your Grandfather's Marijuana. Trends Pharmacol Sci. Mar. 2017;38(3):257-276.

Liu, L. et al., Newly Emerging Drugs of Abuse and Their Detection Methods: An ACLPS Critical Review. Am J Clin Pathol. Jan. 29, 2018;149(2):105-116.

Posthuma-Trumpie, et al. "Lateral flow (immuno)assay: its strengths, weaknesses, opportunities, and threats. A literature review" Anal Bioanal Chem, 2009; 393: 569-82.

Qian, S. et al., Analysis of lateral flow biodetectors: competitive format. Anal Biochem. Mar. 15, 2004;326(2):211-24.

* cited by examiner

FLUID SPECIMEN TESTING

This application claims priority to U.S. provisional patent application Ser. No. 62/857,073, filed Jun. 4, 2019, which is incorporated herein by reference in its entirety.

FIELD

Provided herein is technology relating to testing fluid specimens and particularly, but not exclusively, to apparatuses, devices, methods, systems, and kits for testing a fluid specimen, e.g. urine, saliva, or other body fluids, to detect specified chemical components in the specimen.

BACKGROUND

Employee drug testing typically involves an initial screening test to identify specimens that are negative (e.g., no drugs present). This test is usually performed with a low-cost immunoassay that is very sensitive to small quantities of drug metabolites. If a drug metabolite is detected (referred to as "presumptive positive"), the specimen is then subjected to a confirmation test that typically utilizes a highly specific test method, such as a gas chromatography/mass spectrometry (GC/MS), to identify the specific drug components in the specimen.

Sometimes both the screening and confirmation tests were performed in a common facility such as a centralized testing laboratory. More recently, technologies have been implemented that perform the screening test at a local service site. They typically employ drug test kits similar to home pregnancy test kits, e.g., they detect the presence of one or more specific drug substance in a urine specimen. Such drug test kits generally identify, in human readable form, the drugs being tested and an indication of the presence (or absence) of each drug. The screening test result can either be negative or presumptively positive with respect to each particular drug and/or with respect to the specimen as a whole. If presumptively positive, then the specimen is typically sent to a remote laboratory for confirmation testing.

U.S. Pat. No. 6,342,183 (incorporated herein by reference) describes one apparatus for locally analyzing a specimen to detect specified chemical components. The apparatus includes an assaying device comprising a cup for collecting a fluid specimen and a cap carrying at least one test strip for visually reacting to one or more specified chemical components in the specimen. The assaying device is preferably configured to interact with a reader device capable of reading the reaction of the test strip to produce an electronic data output.

A similar device described in U.S. Pat. No. 6,342,183 (incorporated herein by reference) includes a cup for holding a fluid specimen and a cap to seal the cup. The cap comprises at least one test strip and a plunger for forcing an aliquot of the fluid specimen onto the test strip. A reader device accepts the cup and includes a microprocessor-based controller for actuating the plunger, a camera for producing an image of the test strip, and a processor for analyzing the image to produce test result data. The test result data, along with identification data read from a label carried by the cap, can then be stored or communicated, e.g., via a network or over the internet.

Another similar device described in U.S. Pat. No. 7,537,733 (incorporated herein by reference) describes a system for automatically testing a fluid specimen for the presence of chemical components. The system comprises a collection cup and a cap that carries at least one test strip. The device includes a mechanism to wet the test strip with an aliquot of the fluid specimen. The cup is configured to operate in conjunction with an electronic reader device capable of actuating the mechanism and reading the reaction of the test strip. The reader device comprises a microprocessor-based controller for controlling the camera, actuating the mechanism, and processing the image to produce test result data.

Existing systems often suffer from inconsistencies based on differences in volumes of samples collected and the manner in which the device is used and handled. Improved systems are needed.

SUMMARY

Provided herein is technology relating to testing fluid specimens and particularly, but not exclusively, to apparatuses, devices, methods, systems, and kits for testing a fluid specimen, e.g. urine, saliva, or other body fluids, to detect specified chemical components in the specimen. For example, in some embodiments, the technology provides an assay device (e.g., comprising a cup and a lid) and a reader apparatus adapted to accept the assay device, initiate assay of a sample, and obtain an assay result. Accordingly, the present technology provides an improved system and components thereof for automatically testing a fluid specimen, e.g. urine, saliva, or other body fluids, to indicate for the presence of specified chemical components in the specimen.

In some embodiments, the technology relates to a system comprising an assay device comprising an assay device cup and an assay device lid comprising at least one test strip. The system comprises an integrated aliquot delivery mechanism actuatable to wet the test strip with an aliquot derived from the fluid specimen. In particular, the assay device lid comprises a vent hole that can be in an open state or a closed state. The vent hole in the closed state provides an airlock that prevents sample from flowing to wet the test strip. The vent hole in the open state releases the airlock and provides a metered amount of sample to wet the test strip. The assay device is configured to operate in conjunction with a reader apparatus capable of actuating the aliquot delivery mechanism and reading the reaction of the test strip. In particular, a laser provided by the reader apparatus disrupts a seal covering the vent hole in the closed state to open the vent hole and, accordingly, provide the vent hole in the open state.

In some embodiments, the reader apparatus comprises a keyed receptacle for accommodating a complementary shaped cup housing in a particular orientation. For example, in some embodiments, the reader apparatus comprises a keyed receptacle that is a D-shaped assay device receiver to accommodate (e.g., receive) a D-shaped assay device cup, ensuring proper and consistent orientation of the cup in the reader. Further, the reader apparatus comprises a camera for capturing the image of a test strip, an actuator (e.g., a laser provided by a laser source) for actuating an aliquot delivery mechanism, and a microprocessor configured to control the camera, control the actuator, and to process the image and produce an output for a user.

In some embodiments, the reader apparatus comprises a network connectivity device, e.g. a modem, for enabling communication with a remote host computer. Although each reader apparatus operates independently as a stand-alone device, in some embodiments the system comprises a host computer or server configured to communicate (e.g., by a network) with a plurality of reader devices located at separate service sites. In some embodiments, each service site is configured to operate as a thin client with primary control being exercised by the host computer over the network. Alternatively, in some embodiments, primary control is exercised by the reader device at each site with only high-level supervisory control coming from the host computer.

In some embodiments, the assay device comprises a cap carrying multiple test strips including at least one analyte test strip and at least one adulterant test strip. In some embodiments, the lid is formed of transparent material or comprises a transparent window to permit external viewing of the test strips by the reader apparatus camera. In some embodiments, the lid comprises one or more fiducial marks to facilitate image processing. Further, in some embodiments the lid comprises machine readable identification information (e.g., a bar code) to positively associate the specimen and test results with the correct individual. In some embodiments, the lid does not comprise any human readable indicia identifying the specimen donor or indicating test results.

In some embodiments, the analyte test strip for testing for the presence of specific chemical components in a sample comprises multiple lines (e.g., markings) that become visible when the strip is wetted. In some embodiments, the lines comprise a control or reference line and multiple analyte (e.g., drug) lines related to different chemical components. In use, appearance of all lines within a certain test interval after the strip has been wetted, e.g., up to eight minutes, indicates the absence of the specific analytes assayed by the technology. However, if any of the analytes is present (e.g., at a concentration above a certain threshold), its presence suppresses the appearance of one or more of the lines to indicate the presence of the analytes (e.g., drugs).

In some embodiments, the reader apparatus comprises a camera located so that the assay device lid is imaged onto the camera focal plane (e.g., when the assay device is inserted into the reader apparatus). The reader apparatus comprises a laser source for actuating the assay device lid vent hole (e.g., to release an airlock) to deliver an aliquot of a sample to the test strips. In some embodiments, the reader apparatus comprises a light source to illuminate the lid to enhance the image for the camera.

In some embodiments, the assay device technology finds use as follows: a sample (e.g., a biofluid) is deposited into an assay device cup (e.g., at a local site) and the sample is secured within the assay device cup with the assay device lid (e.g., in a tamper evident fashion). Next, a user (e.g., a test site administrator) places the assay device (e.g., comprising the sample in the assay device cup and secured with the assay device lid) into a reader apparatus (e.g., into a keyed receptacle of a reader apparatus) and enters information relating to the individual providing the sample. In some embodiments, the reader apparatus alerts a host computer (e.g., over a communication network). The sample is assayed in some embodiments by initiating a reader apparatus operational sequence comprising, e.g., recording an image of the assay device lid and, optionally, verifying acceptability to proceed; actuating the laser source to provide a laser to contact the assay device lid label laser target to release an airlock (e.g., to provide the vent hole in an open state) and provide a metered aliquot of the sample to the analyte and adulterant test strips; and recording an image of the assay device lid (e.g., of the test strips and, optionally, adulterant test strips) and, optionally, verifying acceptability to proceed. In some embodiments, additional images of the assay device lid are recorded, e.g., during an assay development interval (e.g., up to approximately eight minutes). Finally, the recorded images of the test strips (e.g., recorded image data) are analyzed to determine the assay results and, optionally, assay validity. In some embodiments, the assay results and, optionally, assay validity, are provided locally, e.g., by displaying the assay results and, optionally, assay validity to a user. In some embodiments, the assay results and, optionally, assay validity, are communicated to a host computer (e.g., over a network). The site administrator then removes the assay device from the reader apparatus.

In some embodiments, the camera produces a digital representation of the image (e.g., of the assay device lid (e.g., of the assay test strips)) that is incident on the camera focal plane. The processor then analyzes the digital representation to determine the color and/or intensity of the adulterant test strip and to locate visible markings on the analyte test strip coincident with the reference and drug lines. In some embodiments, image analysis is performed using fiducial marks on the lid to locate the lid image relative to a reference image. In some embodiments, image analysis comprises, e.g., rotating, translating, and/or scaling the lid image. Thereafter, the digital representation of each test strip is examined to determine the presence (or absence) of drug lines. In some embodiments, examining a test strip comprises locating a test strip reference line by identifying (e.g., drawing) a rectangular region around the reference line. In some embodiments, the rectangular region comprises a rectangular matrix of pixels (e.g., comprising rows and columns of pixels). In some embodiments, each row of the image is examined to determine whether a pixel at each column position exceeds a threshold. In some embodiments, the sum of pixels exceeding the threshold is determined for each row. In some embodiments, the row sums are used to produce a plot comprising an X-axis that is related to the height (e.g., number of rows) of the region and a Y-axis that is related to the values of the individual row sums. In some embodiments, the plot produces a bell-shaped curve comprising a peak that indicates the reference line. If no reference line is located, the test is terminated. If the reference line is located, then the examination continues to locate the drug lines. In some embodiments, image analysis is used to detect drug lines that vary in amplitude due to variations in, e.g., wetting uniformity, urine color, variations amongst test strips, exposure time, etc. In some embodiments, analysis of the images compensates for these variations, e.g., by dividing each drug line into a left, a center, and a right portion. A drug line is presumed to occupy the center portion of each region. However, its exact position and exact width can vary due to the aforementioned factors. Moreover, its brightness difference in relation to neighboring areas can be very subtle. Hence, a procedure is used to determine the weight of a line on a relative basis. For example, in some embodiments (e.g., for each drug region plot), the total area under each of the three regions (left, center, right) is calculated. The left and right region areas are then numerically summed, and this resulting total area sum is multiplied by an empirically determined weighting value to produce a weighted sum. If the area of the center region is less than or equal to the weighted sum, no line is present. In some embodiments, the technology comprises use of a weighting value of 0.75 that has been experimentally determined to produce very acceptable results using urine samples with known drug concentrations.

In some embodiments, the technology provides an assay device for detecting an analyte. In some embodiments, the assay device comprises an assay device cup and an assay device lid, wherein said assay device cup is configured to hold a sample and said assay device lid comprises a test strip and a vent hole that is actuatable to release an airlock and provide a metered amount of said sample to said test strip.

As used herein, the term "metered amount" refers to a volume of a sample that is controlled, predictable, and substantially reproducible (e.g., less than approximately 5-25% variation in sample volume (e.g., less than 25, 24, 23, 22, 21, 20, 19, 18, 17, 16, 15, 14, 13, 12, 11, 10, 9, 8, 7, 6, or 5% variation in sample volume)). In some embodiments, a "metered amount" refers to a volume of a sample that is controlled, predictable, and substantially reproducible, e.g., varies less than approximately 10% in sample volume (e.g., less than approximately 10.0, 9.5, 9.0, 8.5, 8.0, 7.5, 7.0, 6.5, 6.0, 5.5, 5.0, 4.5, 4.0, 3.5, 3.0, 2.5, 2.0, 1.5, 1.0, or 0.5 variation in sample volume) over multiple uses of the assay device.

In some embodiments, the assay device further comprises an adulterant test strip. In some embodiments, the assay device lid comprises a shape (e.g., a D-shape) that is complementary to an assay device receiver (e.g., a D-shaped assay device receiver) of a reader apparatus and said assay device lid compels insertion of the assay device into the reader apparatus in a particular orientation. In some embodiments, the assay device lid comprises a label sealing the vent hole and comprising a laser target. In some embodiments, the assay device lid comprises a label comprising an adhesive tab configured to provide a tamper-evident seal for the assay device. In some embodiments, the assay device lid comprises a label comprising a barcode. In some embodiments, the assay device lid comprises a test strip viewing window providing imaging access to said test strip. In some embodiments, the assay device comprises a gasket that retains said test strip in said assay device lid and that is configured to seal said sample in said assay device when said assay device lid is engaged with said assay device cup. In some embodiments, the sample is a biological sample (e.g., a biofluid (e.g., urine)). In some embodiments, the analyte is a drug (e.g., a drug of abuse).

In some embodiments the technology relates to an assay system for detecting an analyte. In some embodiments, the assay system comprises an assay device comprising an assay device cup and an assay device lid, wherein said assay device cup is configured to hold a sample and said assay device lid comprises a test strip and a vent hole that is actuatable to release an airlock and provide a metered amount of said sample to said test strip; and a reader apparatus comprising a piercing means configured to actuate said vent hole. In some embodiments, the piercing means is a laser. In some embodiments, the assay device lid comprises a shape (e.g., a D-shape) that is complementary to an assay device receiver (e.g., comprising a D-shape) of said reader apparatus and said assay device lid compels insertion of the assay device into the reader apparatus in a particular orientation. In some embodiments, the sample is a biological sample (e.g., a biological fluid (e.g., urine)). In some embodiments, the analyte is a drug (e.g., a drug of abuse). In some embodiments, the comprises a channel configured to wet a bottom portion of said test strip with a metered amount of said sample. In some embodiments, the assay device lid comprises a label comprising an adhesive tab configured to provide a tamper-evident seal for the assay device. In some embodiments, the reader apparatus comprises an imaging component (e.g., a camera) configured to record an image of said test strip. In some embodiments, the assay device lid compels insertion of the assay device into the reader apparatus in a particular orientation for recording an image of said test strip. In some embodiments, the reader apparatus comprises a microprocessor. In some embodiments, the reader apparatus comprises a microprocessor configured to control a laser source and/or an imaging component. In some embodiments, the reader apparatus comprises a software component configured to identify a test result line on said test strip. In some embodiments, the reader apparatus comprises a software component configured to quantify a test result line on said test strip. In some embodiments, the apparatus comprises a software component configured to report a test result to a user. In some embodiments, the reader apparatus comprises a software component configured to communicate a test result over a network. In some embodiments, the reader apparatus comprises an input component configured to accept input from a user (e.g., data identifying the sample, an individual who provided a sample, a test to be performed by said reader apparatus). In some embodiments, the reader apparatus comprises a removable reservoir to contain leaks.

In some embodiments, the technology provides a method for detecting the presence of an analyte in a sample. In some embodiments, the method comprises providing a sample in an assay device comprising an assay device lid and an assay device cup, wherein said assay device lid comprises a test strip and an actuatable vent hole sealed by a label; actuating said vent hole to release an airlock to provide a metered amount of said sample to said test strip; obtaining a test result by viewing or imaging said test strip. In some embodiments, actuating said vent hole comprises contacting said label of said assay device lid with a laser. In some embodiments, obtaining a test result comprises imaging said test strip with a camera. In some embodiments, methods further comprise inserting said assay device into a reader apparatus. In some embodiments, the reader apparatus comprises a laser source and an imaging component. In some embodiments, providing a sample comprises urinating into said assay device cup and engaging said assay device lid with said assay device cup to seal said sample in said assay device. In some embodiments, the assay device further comprises a gasket configured to seal said sample in said assay device. In some embodiments, the sample is a biological sample (e.g., urine). In some embodiments, the analyte is a drug (e.g., a drug of abuse). In some embodiments, the method further comprises communicating a test result to a user. In some embodiments, the method further comprises communicating a test result over a network.

In some embodiments, the technology provides a kit comprising an assay device as described herein.

The technology finds use in a number of research and clinical applications. For example, in some embodiments the technology finds use to detect the presence, absence, concentration, and/or amount of an analyte in a sample. In some embodiments, the technology finds use to test a urine sample of an employee by an employer. In some embodiments, the technology finds use to test a urine sample of a person in a drug abuse recovery program.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 4A is a drawing of an assay device lid 120 comprising an assay device lid tab 122e and an assay device lid gasket 123. The assay device lid gasket 123 comprises an assay device lid gasket inlet hole 123a.

FIG. 4B is a drawing of an assay device lid 120 comprising an assay device lid tab 122e and an assay device lid label laser target 122a.

FIG. 5A is an exploded drawing of an assay device lid comprising an assay device lid body 121, an assay device lid label 122, an assay device lid gasket 123, and an assay device test strip panel 124. The assay device lid gasket 123 comprises an assay device lid gasket inlet hole 123a.

FIG. 9 is a drawing of an assay device lid 120 comprising an assay device lid gasket 123. The assay device lid gasket 123 comprises an assay device lid gasket inlet hole 123a.

Figure 1A:
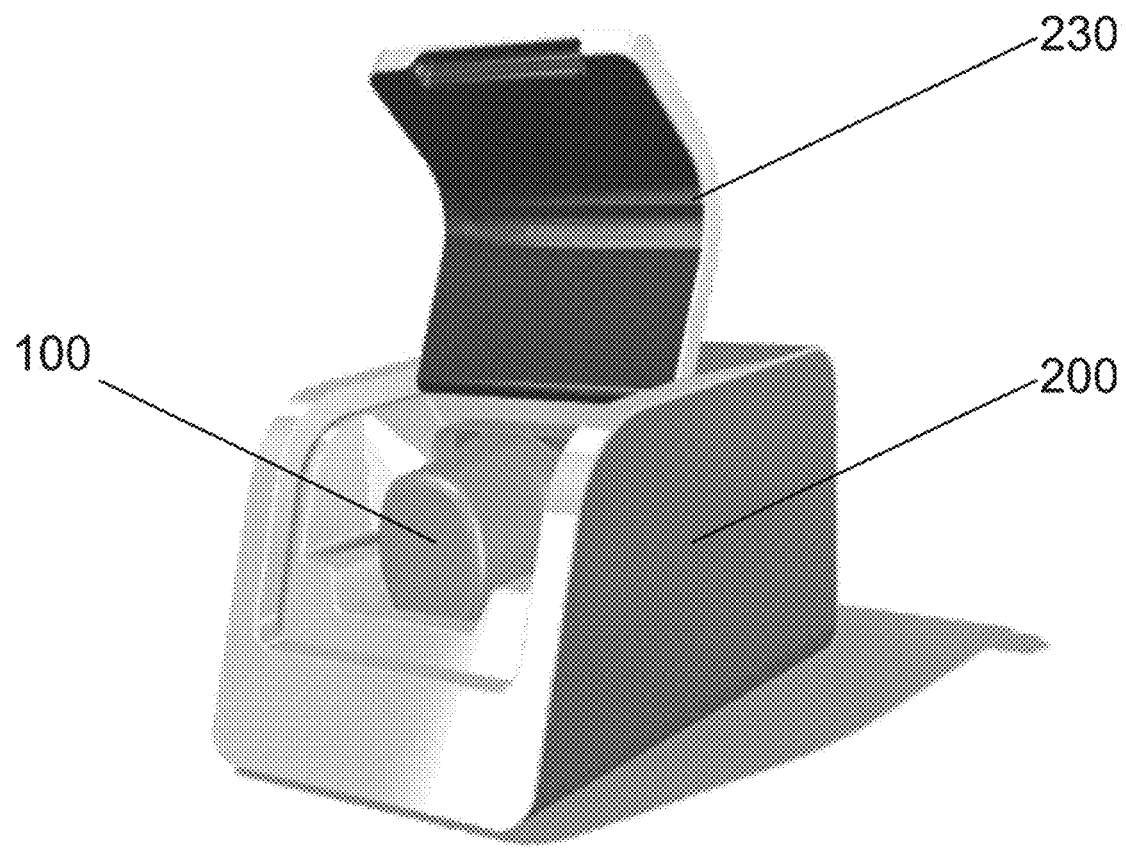
FIG. 1A is a drawing of a reader apparatus 200 with a reader apparatus lid 230 in an open state. The reader apparatus comprises an inserted assay device 100.
Figure 1B:
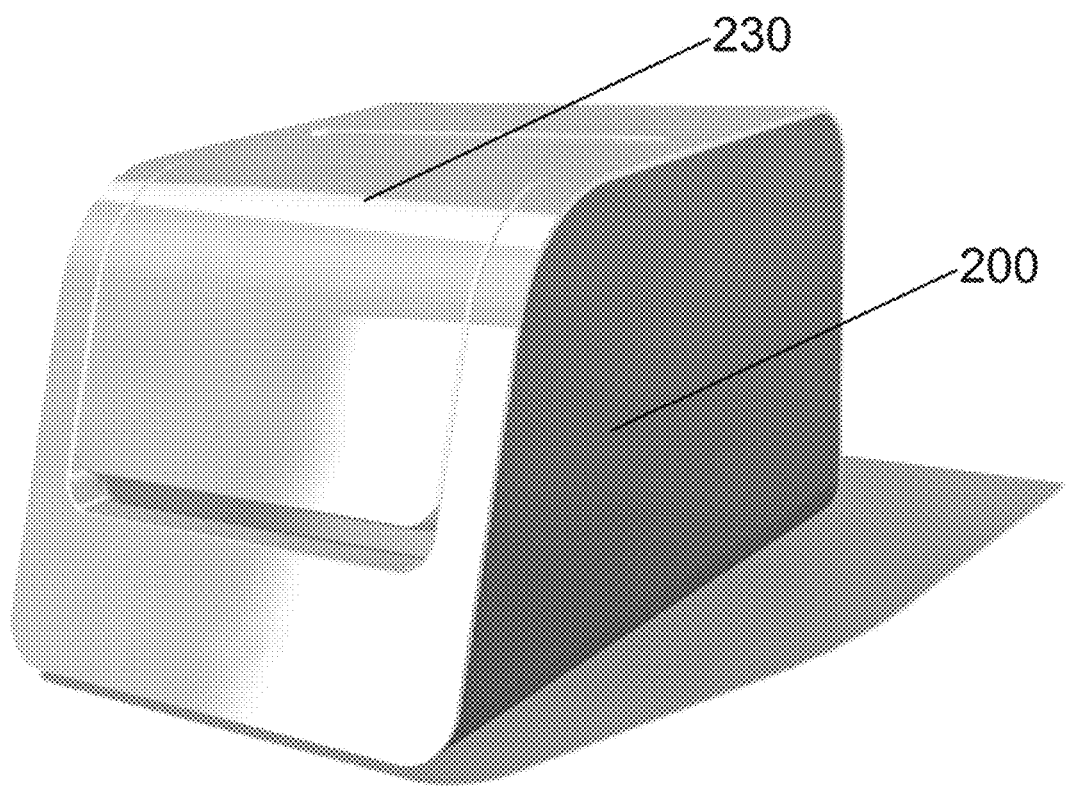
FIG. 1B is a drawing of a reader apparatus 200 with a reader apparatus lid 230 in a closed state.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to testing fluid specimens and particularly, but not exclusively, to apparatuses, devices, methods, systems, and kits for testing a fluid specimen, e.g. urine, saliva, or other body fluids, to detect specified chemical components in the specimen.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the terms "about", "approximately", "substantially", and "significantly" are understood by persons of ordinary skill in the art and will vary to some extent on the context in which they are used. If there are uses of these terms that are not clear to persons of ordinary skill in the art given the context in which they are used, "about" and "approximately" mean plus or minus less than or equal to 10% of the particular term and "substantially" and "significantly" mean plus or minus greater than 10% of the particular term.

As used herein, disclosure of ranges includes disclosure of all values and further divided ranges within the entire range, including endpoints and sub-ranges given for the ranges.

As used herein, the suffix "-free" refers to an embodiment of the technology that omits the feature of the base root of the word to which "-free" is appended. That is, the term "X-free" as used herein means "without X", where X is a feature of the technology omitted in the "X-free" technology. For example, a "calcium-free" composition does not comprise calcium, a "mixing-free" method does not comprise a mixing step, etc.

Although the terms "first", "second", "third", etc. may be used herein to describe various steps, elements, compositions, components, regions, layers, and/or sections, these steps, elements, compositions, components, regions, layers, and/or sections should not be limited by these terms, unless otherwise indicated. These terms are used to distinguish one step, element, composition, component, region, layer, and/or section from another step, element, composition, component, region, layer, and/or section. Terms such as "first", "second", and other numerical terms when used herein do not imply a sequence or order unless clearly indicated by the context. Thus, a first step, element, composition, component, region, layer, or section discussed herein could be termed a second step, element, composition, component, region, layer, or section without departing from technology.

As used herein, the word "presence" or "absence" (or, alternatively, "present or "absent") is used in a relative sense to describe the amount or level of a particular entity (e.g., an analyte). For example, when an analyte is said to be "present" in a sample, it means the level or amount of the analyte is above a pre-determined threshold; conversely, when an analyte is said to be "absent" in a test sample, it means the level or amount of the analyte is below a pre-determined threshold. The pre-determined threshold may be the threshold for detectability associated with the particular assay used to detect the analyte or any other threshold. When an analyte is "detected" in a sample it is "present" in the sample; when an analyte is "not detected" it is "absent" from the sample. Further, a sample in which an analyte is "detected" or in which the analyte is "present" is a sample that is "positive"

for the analyte. A sample in which an analyte is "not detected" or in which the analyte is "absent" is a sample that is "negative" for the analyte.

As used herein, an "increase" or a "decrease" refers to a detectable (e.g., measured) positive or negative change in the value of a variable relative to a previously measured value of the variable, relative to a pre-established value, and/or relative to a value of a standard control. In some embodiments, an increase is a positive change, preferably at least 10%, more preferably 50%, still more preferably 2-fold, even more preferably at least 5-fold, and most preferably at least 10-fold relative to the previously measured value of the variable, the pre-established value, and/or the value of a standard control. Similarly, a decrease is a negative change, preferably at least 10%, more preferably 50%, still more preferably at least 80%, and most preferably at least 90% of the previously measured value of the variable, the pre-established value, and/or the value of a standard control. Other terms indicating quantitative changes or differences, such as "more" or "less," are used herein in the same fashion as described above.

As used herein, the term "system" denotes a set of components, real or abstract, comprising a whole where each component interacts with or is related to at least one other component within the whole.

As used herein, the term "assaying" refers to qualitatively or quantitatively testing a sample for an analyte (e.g., for the presence, absence, concentration, and/or amount of the analyte). Assaying may comprise an immunological test, a chemical test, an enzymatic test, and the like. In some embodiments, the present technology assays for the presence, absence, concentration, and/or amount of a variety of analytes such as but not limited to, a chemical, an organic compound, an inorganic compound, a metabolic product, a drug or a drug metabolite, an organism or a metabolite of such an organism, a nucleic acid, a protein, a hormone, or a combination thereof. Assaying may involve comparing the results obtained against a positive or negative control as is common in the biochemical and immunological arts. When determining the concentration of an analyte, the assay may also include at least one quantitative control to determine the amount of analyte present and may further include mathematical calculations such as comparing the amount of analyte to the volume within the collection container or reservoir.

As used herein, the term "test strip" and "test element" are used interchangeably to refer to a device for detecting the presence, absence, concentration, and/or amount of an analyte in a sample or specimen. Test strips of the present technology include but are not limited to lateral flow detection devices (e.g., assay strip devices). In lateral flow detection devices, the liquid sample or specimen moves through a matrix or material by lateral flow or capillary action. An exemplary lateral flow test device is an immunochromatographic device. In a typical immunochromatographic device the sample moves through a sample application zone, a reagent zone, and a detection zone. The sample application zone is a region of the lateral flow detection device that is contacted first by the sample; the reagent zone is a region in which particular reagents for the desired assay are positioned such that they migrate with an analyte along the device; and the detection zone is a region in which the results of the assay are visualized, presented, and/or determined. In some embodiments, a mobilizable reagent such as a labeled antibody is provided in the reagent zone and an immobilized reagent is provided in the detection zone. A lateral flow detection device may be used in a substantially vertical or a substantially horizontal orientation or in an orientation substantially between vertical and horizontal. Preferably, neither a reagent zone nor a detection zone contacts the sample or analyte unless the sample or analyte migrates along the lateral flow detection device. Persons knowledgeable in the art commonly refer to a lateral flow detection device using terms such as "immunochromatographic", "dip stick", and "membrane technology".

As used herein, the term "analyte" refers to a compound or composition to be detected or measured. An analyte is generally capable of binding to a ligand, a receptor, or an enzyme. The analyte may be an antibody or antigen such as a protein or drug, or a metabolite. The precise nature of antigenic and drug analytes together with numerous examples thereof are disclosed in U.S. Pat. No. 4,299,916, particularly columns 16 to 23, and in U.S. Pat. No. 4,275,149, particularly columns 17 and 18, each of which is incorporated herein by reference. Analytes can include antibodies and receptors, including active fragments or fragments thereof. An analyte can include an analyte analogue, which is a derivative of an analyte, such as, for example, an analyte altered by chemical or biological methods, such as by the action of reactive chemicals, such as adulterants or enzymatic activity. An analyte can be but is not limited to a drug, a drug of abuse, a hormone, a protein, a nucleic acid, an element, an ion, a small molecule (e.g., a natural or synthetic small molecule), an etiological agent, or a specific binding member.

As used herein, the term "sample" or "specimen" refers to any material to be assayed for the presence, absence, concentration, and/or amount of an analyte. Preferably, a sample is a fluid sample such as a liquid sample. Examples of liquid samples that may be assayed include bodily fluids (e.g., blood, serum, plasma, saliva, urine, ocular fluid, semen, sputum, sweat, tears, and spinal fluid), water samples (e.g., samples of water from oceans, seas, lakes, rivers, and the like), samples from home, municipal, or industrial water sources, runoff water, or sewage samples; and food samples (e.g., milk, beer, juice, or wine). Viscous liquid, semisolid, or solid specimens may be used to create liquid solutions, eluates, suspensions, or extracts that can be samples. For example, throat or genital swabs may be suspended in a liquid solution to make a sample. Samples can include a combination of liquids, solids, gasses, or any combination thereof (e.g., a suspension of lysed or unlysed cells in a buffer or solution). Samples can comprise biological materials, such as cells, microbes, organelles, and biochemical complexes. Liquid samples can be made from solid, semisolid, or highly viscous materials, such as soils, fecal matter, tissues, organs, biological fluids, or other samples that are not fluid in nature. For example, solid or semisolid samples can be mixed with an appropriate solution, such as a buffer, a diluent, and/or extraction buffer. The sample can be macerated, frozen and thawed, or otherwise extracted to form a fluid sample. Residual particulates may be removed or reduced using conventional methods, such as filtration or centrifugation.

DESCRIPTION

Provided herein is technology relating to testing fluid specimens and particularly, but not exclusively, to apparatuses, devices, methods, systems, and kits for testing a fluid specimen, e.g. urine, saliva, or other body fluids, to detect specified chemical components in the specimen.

Apparatuses and Devices

In some embodiments, the technology provides an assay device 100 and a reader apparatus 200 (see, e.g., FIG. 1). In some embodiments, the assay device comprises an assay device cup 110 and an assay device lid 120 (see, e.g., FIG. 2A and FIG. 2B). The assay device cup is configured to accept a sample and retain the sample for testing (e.g., by the reader apparatus).

The assay device cup 110 defines an interior volume for collecting a fluid specimen, e.g., a body fluid such as urine. After the fluid specimen has been deposited into the cup, the lid is mounted thereon to seal the interior volume and prevent the fluid specimen from leaking. In some embodiments, each assay device is used only once, e.g., to collect a single specimen. Accordingly, in some embodiments, the assaying device components are fabricated via relatively low-cost plastic molding processes.

Figure 10:
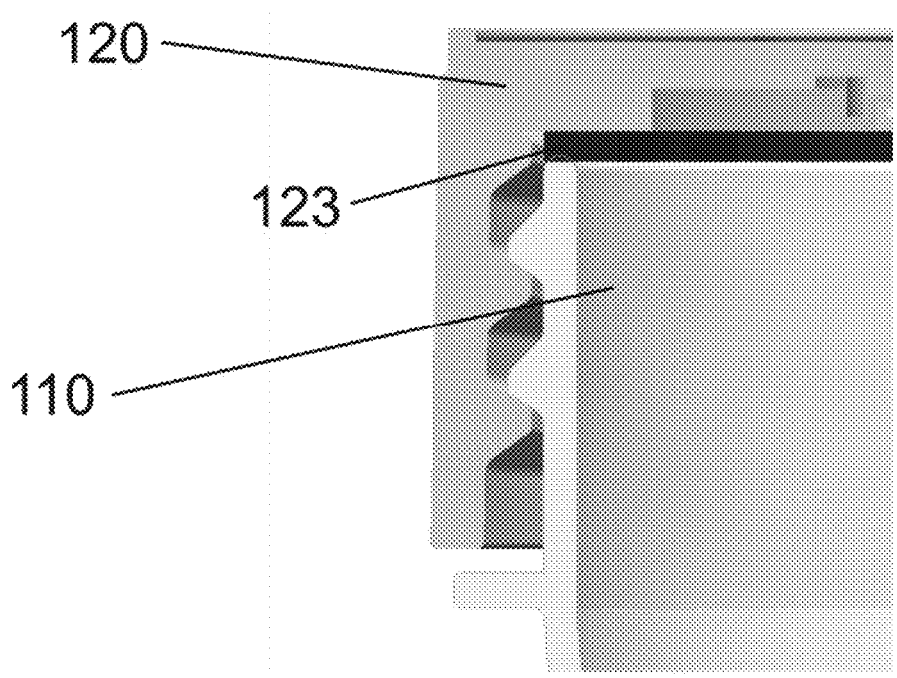
FIG. 10 is a close-up drawing of an assay device lid 120 covering an assay device cup 110 (e.g., by engaging threads of the assay device lid 120 with threads of the assay device cup 110 (e.g., by screwing the assay device lid 120 onto the assay device cup 110)). Engaging the assay device lid 120 with the assay device cup 110 compresses the assay device lid gasket 123 between the assay device lid 120 and the assay device cup 110. In some embodiments, the technology comprises use of one (e.g., a single) gasket (e.g., foam gasket) that both seals the test strips into the lid and seals the lid onto the cup.
Figure 11:
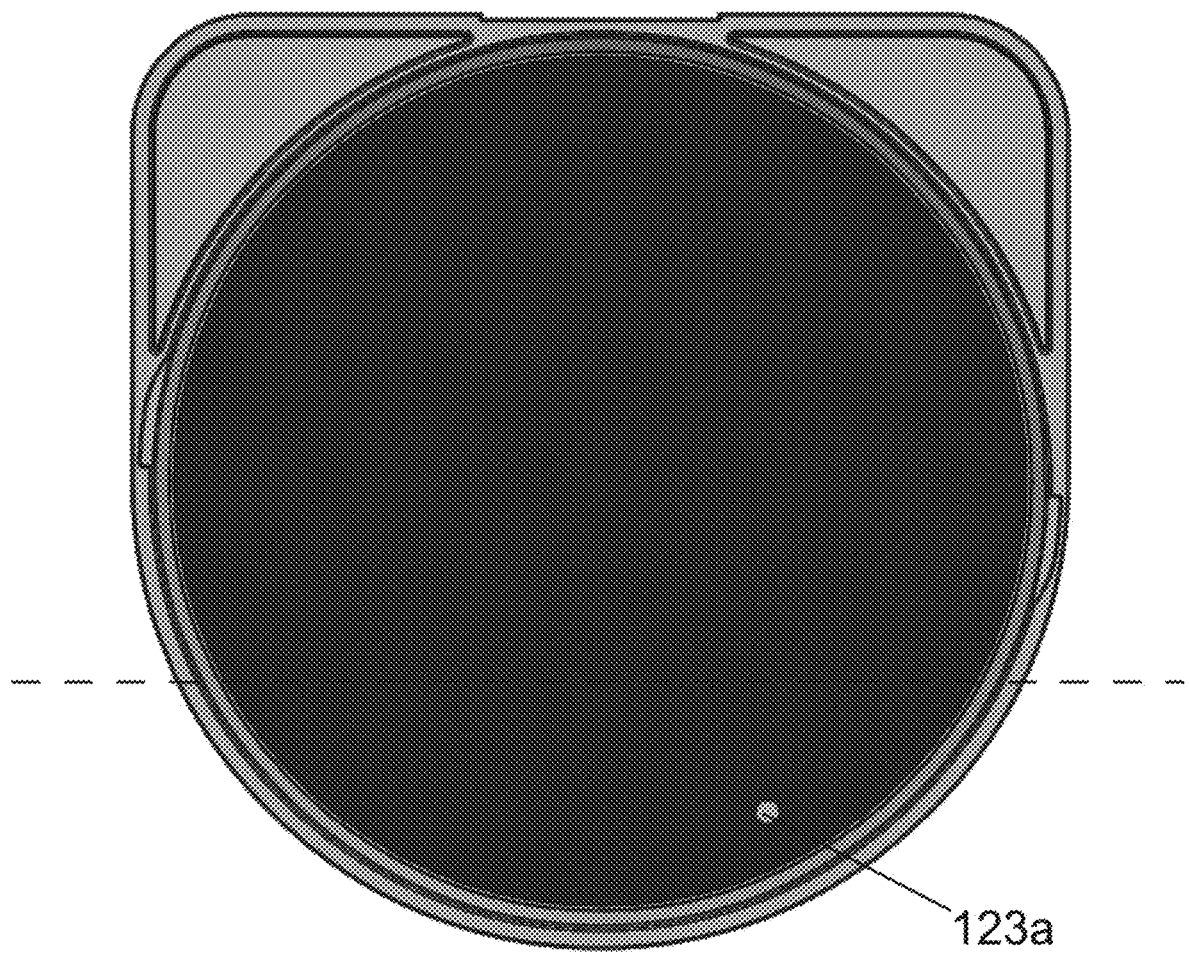
FIG. 11 is a drawing of an assay device lid showing the assay device lid gasket inlet hole 123a. The dotted line shows the maximum liquid height when a sample has been introduced into the device according to embodiments of the technology described herein.

The assay device lid provides a number of functions. For example, the assay device lid is configured to engage with and seal the assay device cup (see, e.g., FIG. 10), e.g., to securely retain a sample in the assay device. In addition, the assay device lid comprises test strips for contacting a sample and providing a visual signal indicating a test result. The assay device lid also comprises a channel and vent hole configured to provide a metered amount of a sample to the test strips as described herein. In some embodiments, the assay device lid has a D-shape to ensure that the assay device is properly inserted into a reader apparatus (e.g., comprising a complementary D-shaped assay device receiver).

The assay device lid is either transparent or comprises one or more transparent areas, e.g., windows, for enabling a test strip mounted beneath to be visible therethrough. As will be discussed hereinafter, the lid comprises components to accommodate one or more test strips that, when wetted by a fluid specimen, react to provide a visual indication indicative of a characteristic of the specimen (e.g., presence, absence, concentration, and/or amount of an analyte). A test strip viewing window 122b covers test strips intended to detect various analytes, e.g., typically associated with illegal substance abuse. In some embodiments, if the strip is being used to test for the presence of specific analytes, the presence of such analytes will suppress the appearance of one or more visual lines. In some embodiments, if all lines visually appear within a certain test interval, e.g., up to eight minutes after the test strip has been wetted, this will indicate the absence of the analytes. However, if an analyte is present in a concentration above a certain threshold, their presence will suppress the appearance of one or more of the lines to indicate to a computer-based reader the presence of such chemical components.

In some embodiments, the assay device lid comprises adulterant test strips intended to detect specimen authenticity and adulteration. As is well known, a freshly voided urine specimen can be authenticated by sensing various characteristics including its temperature, specific gravity, and creatinine content. Adulteration of the specimen can be detected by known adulteration test strips sensitive to exogenous components.

Figure 3:
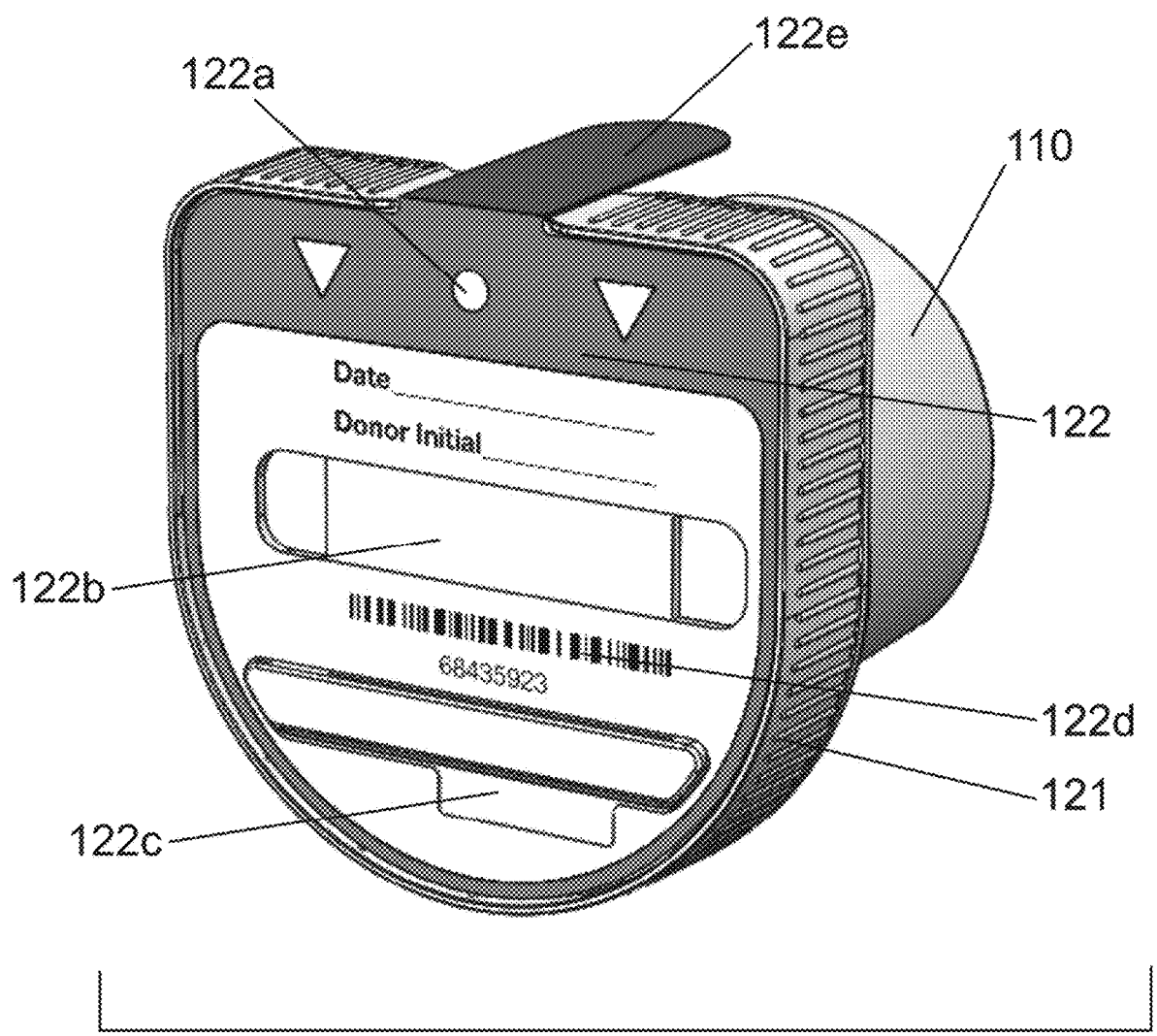
FIG. 3 is a drawing of an assay device 100 comprising an assay device cup 110 and an assay device lid. The assay device lid comprises an assay device lid body 121 and an assay device lid label 122. The assay device lid label 122 comprises an assay device lid label laser target 122a, an assay device lid label test strip viewing window 122b, an assay device lid label adulterant viewing window 122c, an assay device lid label barcode 122d, and an assay device lid tab 122e. In the embodiment of the assay device lid shown in FIG. 3, the assay device lid 120 has a "D" shape, e.g., the assay device lid 120 comprises a rounded portion and a flat portion.
Figure 4A:
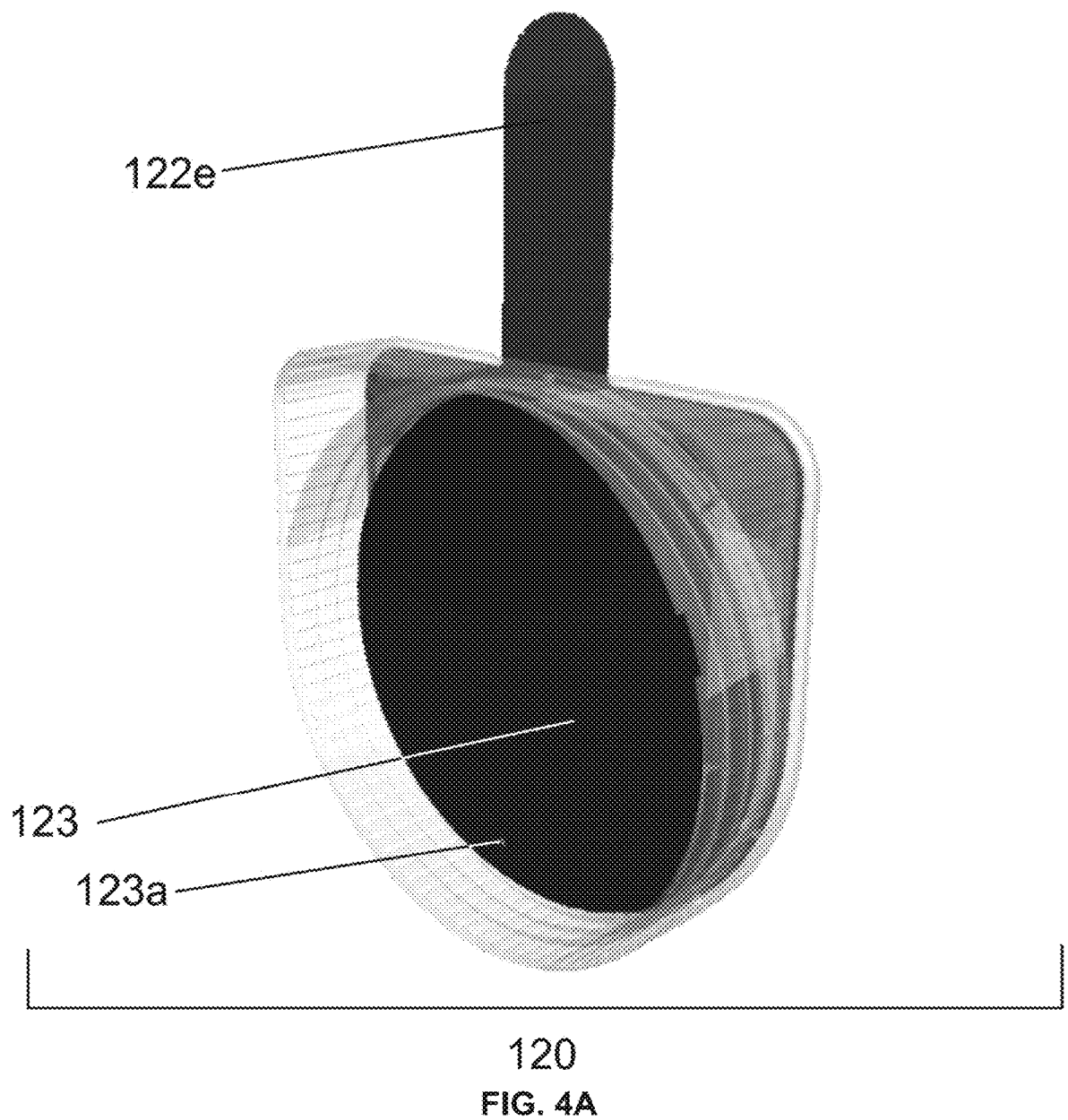
Figure 4B:
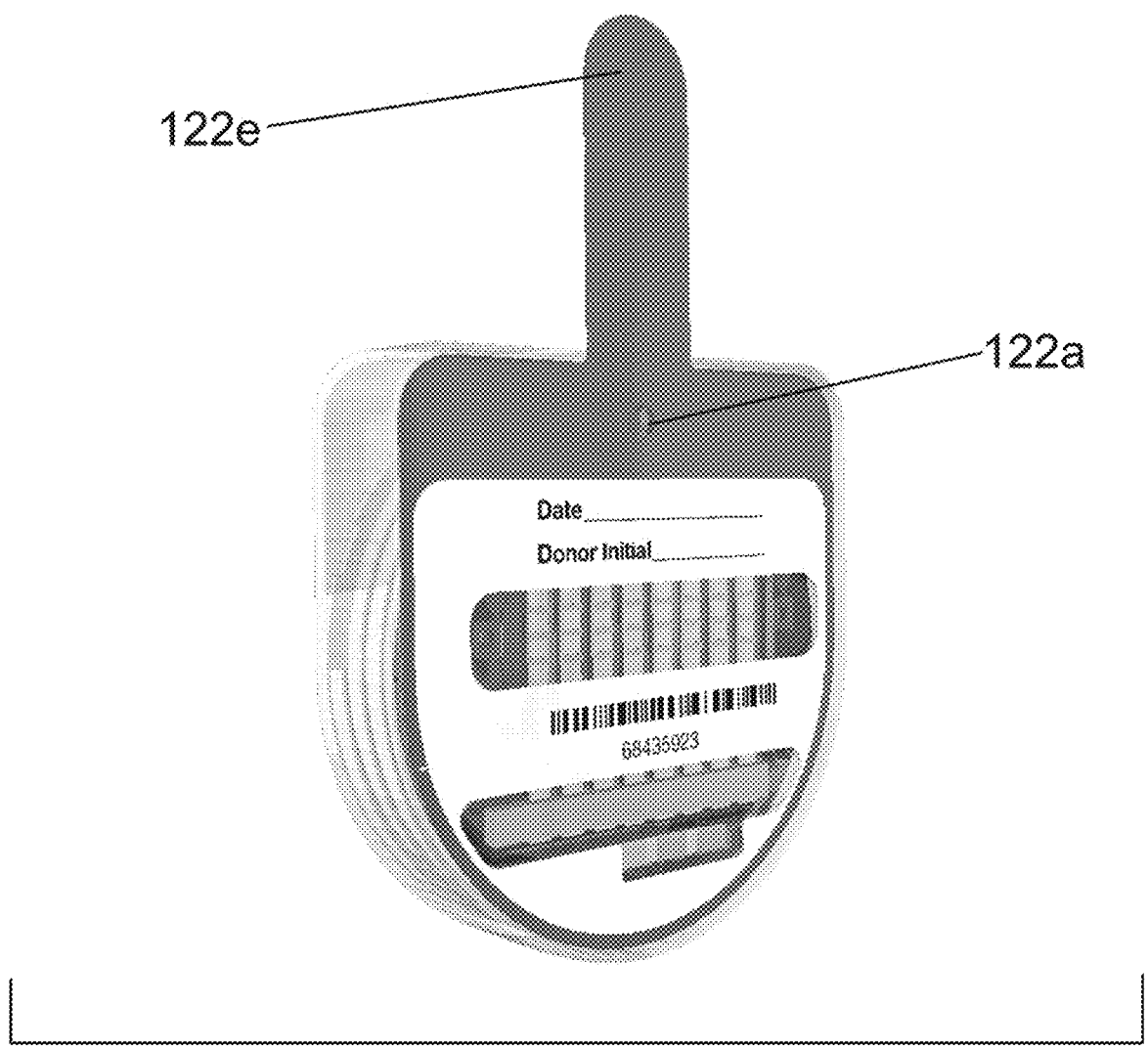
Figure 5A:
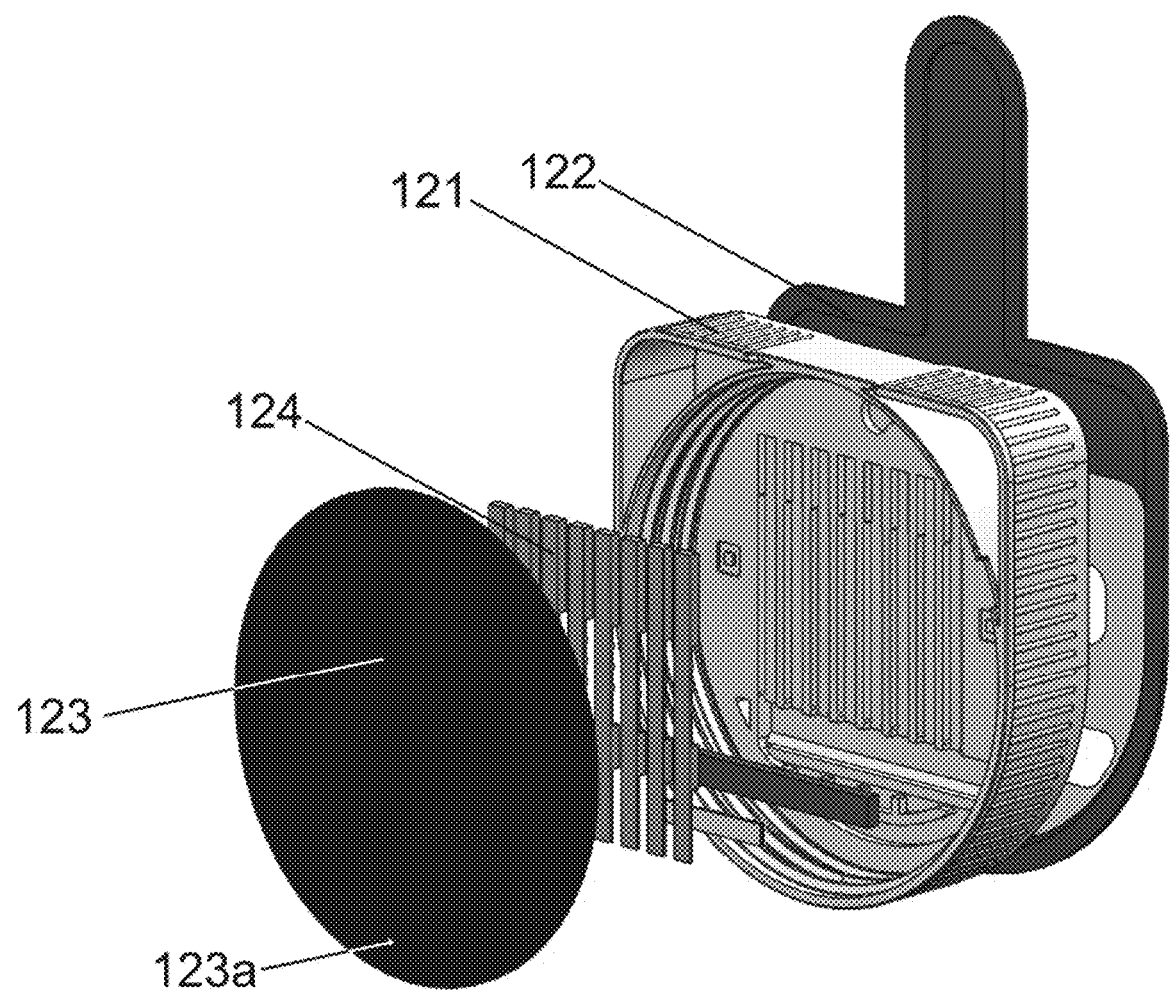
Figure 5B:
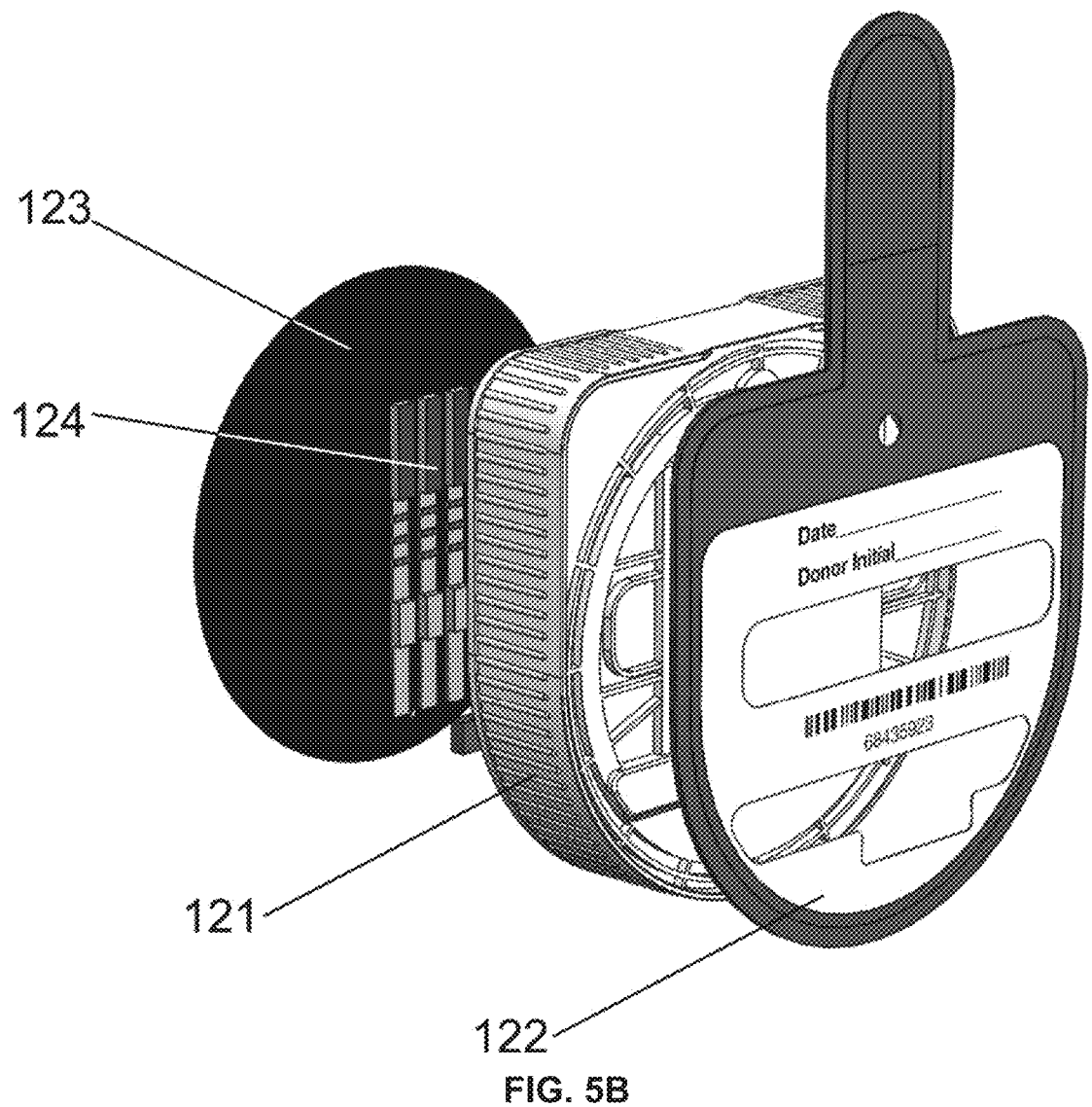
FIG. 5B is an exploded drawing of an assay device lid comprising an assay device lid body 121, an assay device lid label 122, an assay device lid gasket 123, and an assay device test strip panel 124.
Figure 7:
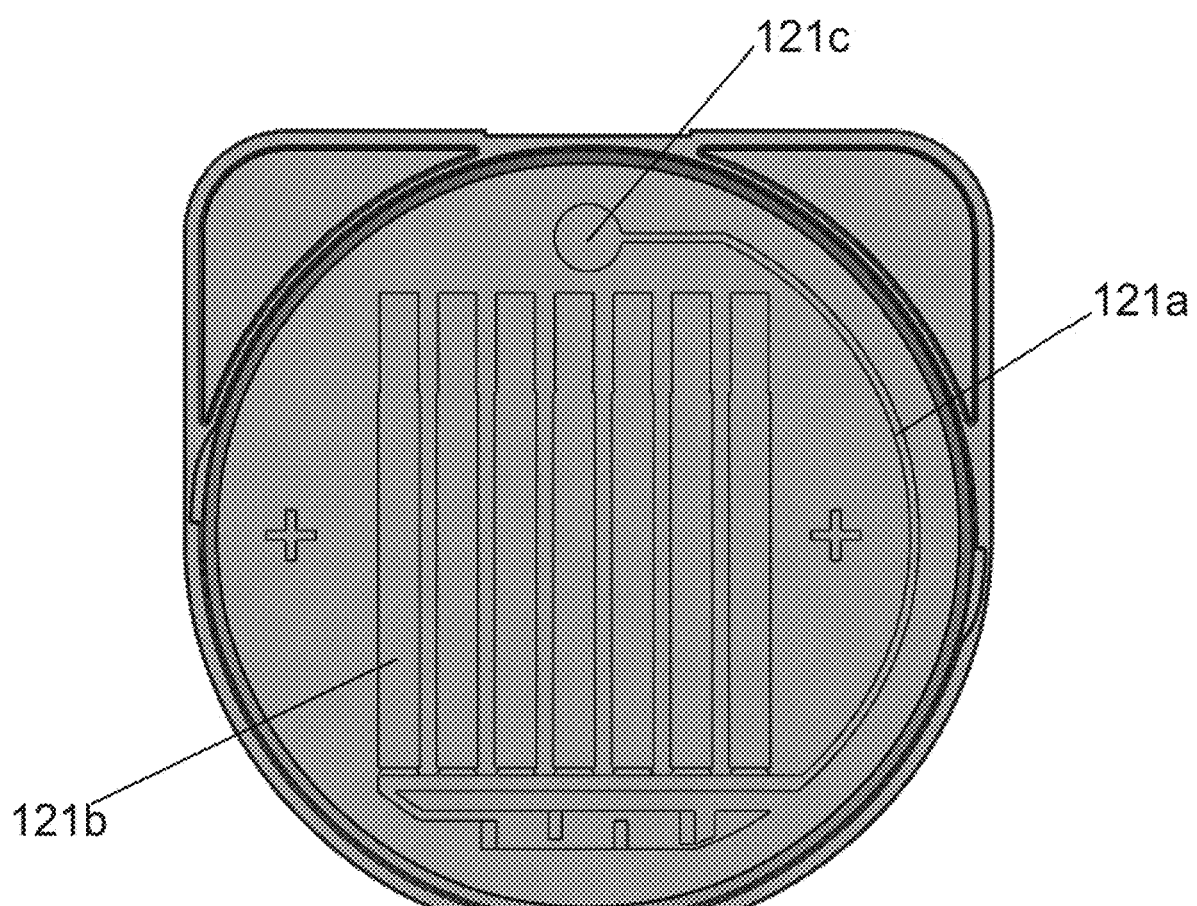
FIG. 7 is a drawing of an assay device lid body comprising an assay device lid body channel 121a, an assay device lid body test strip receptacle 121b (e.g., a plurality of lid body test strip receptacles), and an assay device lid body vent hole 121c. In the embodiment of the assay device lid body shown in FIG. 7, the assay device lid body vent hole 121c is covered by the assay device lid label (e.g., the assay device lid label laser target region) to provide the assay device lid body vent hole 121c in a closed state.
Figure 8:
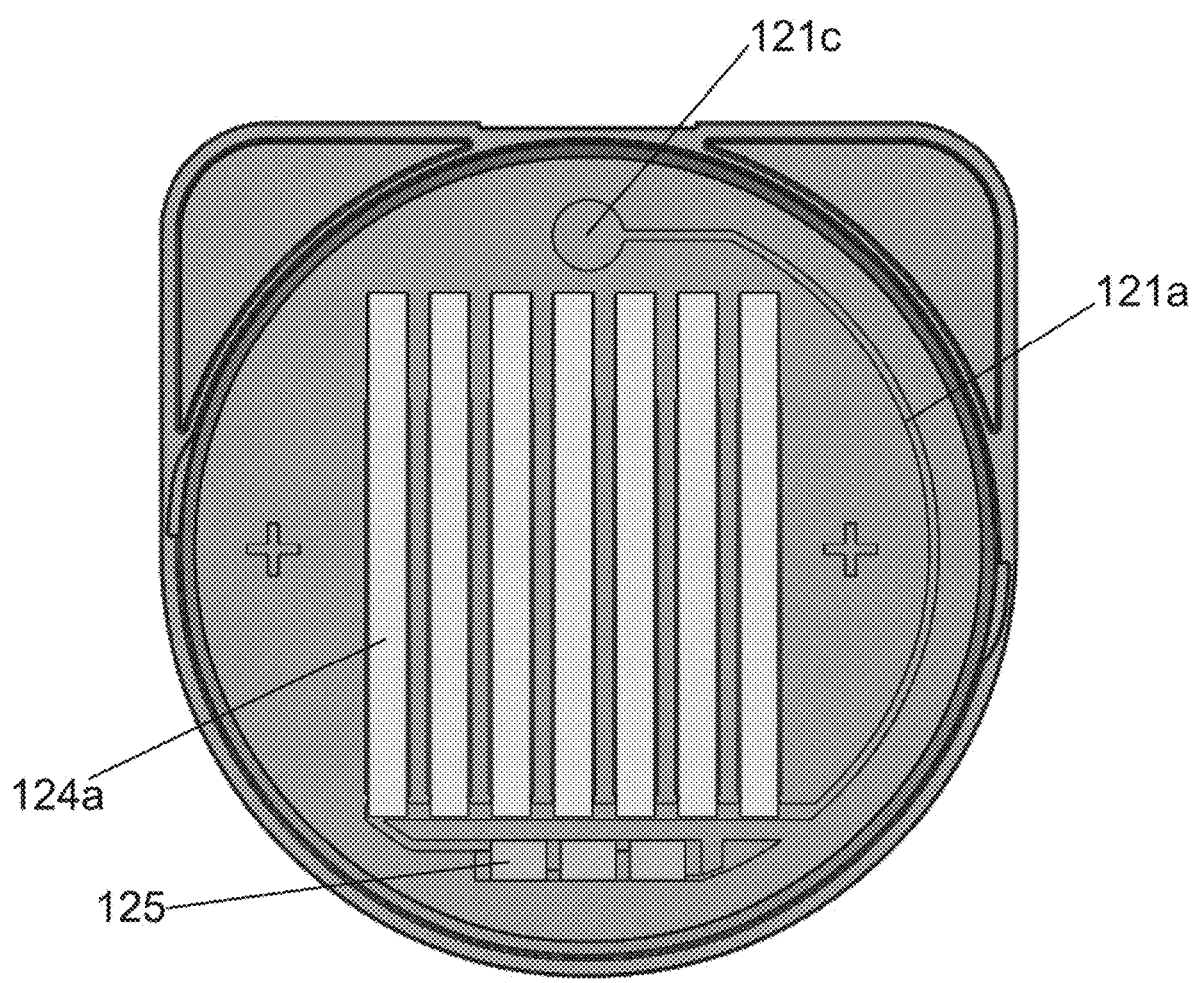
FIG. 8 is a drawing of an assay device lid body comprising an assay device lid body channel 121a, an assay device test strip 124a (e.g., placed in an assay device test strip receptacle), an assay device lid body vent hole 121c, and an assay device adulterant test strip 125 (e.g., a plurality of assay device adulterant test strips). In the embodiment of the assay device lid body shown in FIG. 8, the assay device lid body vent hole 121c is covered by the assay device lid label (e.g., the assay device lid label laser target region) to provide the assay device lid body vent hole 121c in a closed state.
Figure 12:
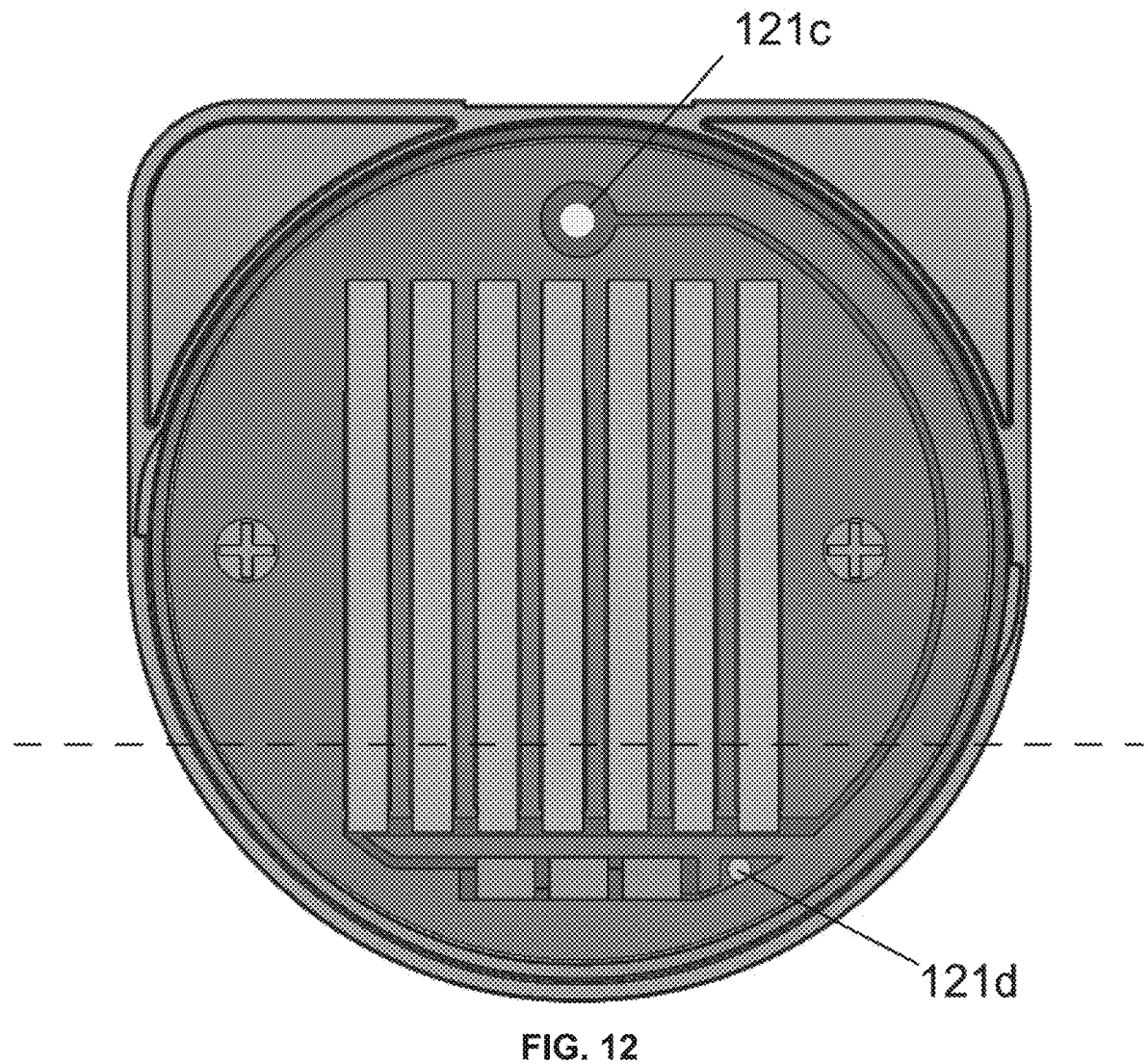
FIG. 12 is a drawing of an assay device lid showing the assay device lid body vent hole 121c and the assay device lid body inlet hole 121d. In the embodiment of the assay device lid shown in FIG. 12, a laser has formed a hole in the assay device lid label (e.g., in the assay device lid label laser target area) to provide the assay device lid body vent hole 121c in an open state. When the assay device lid body vent hole 121c is in an open state, an airlock is released and sample flows from the assay device cup through the assay device lid body inlet hole 121d into the assay device lid body channel. The dotted line shows the maximum liquid height when a sample has been introduced into the device according to embodiments of the technology described herein.
Figure 13:
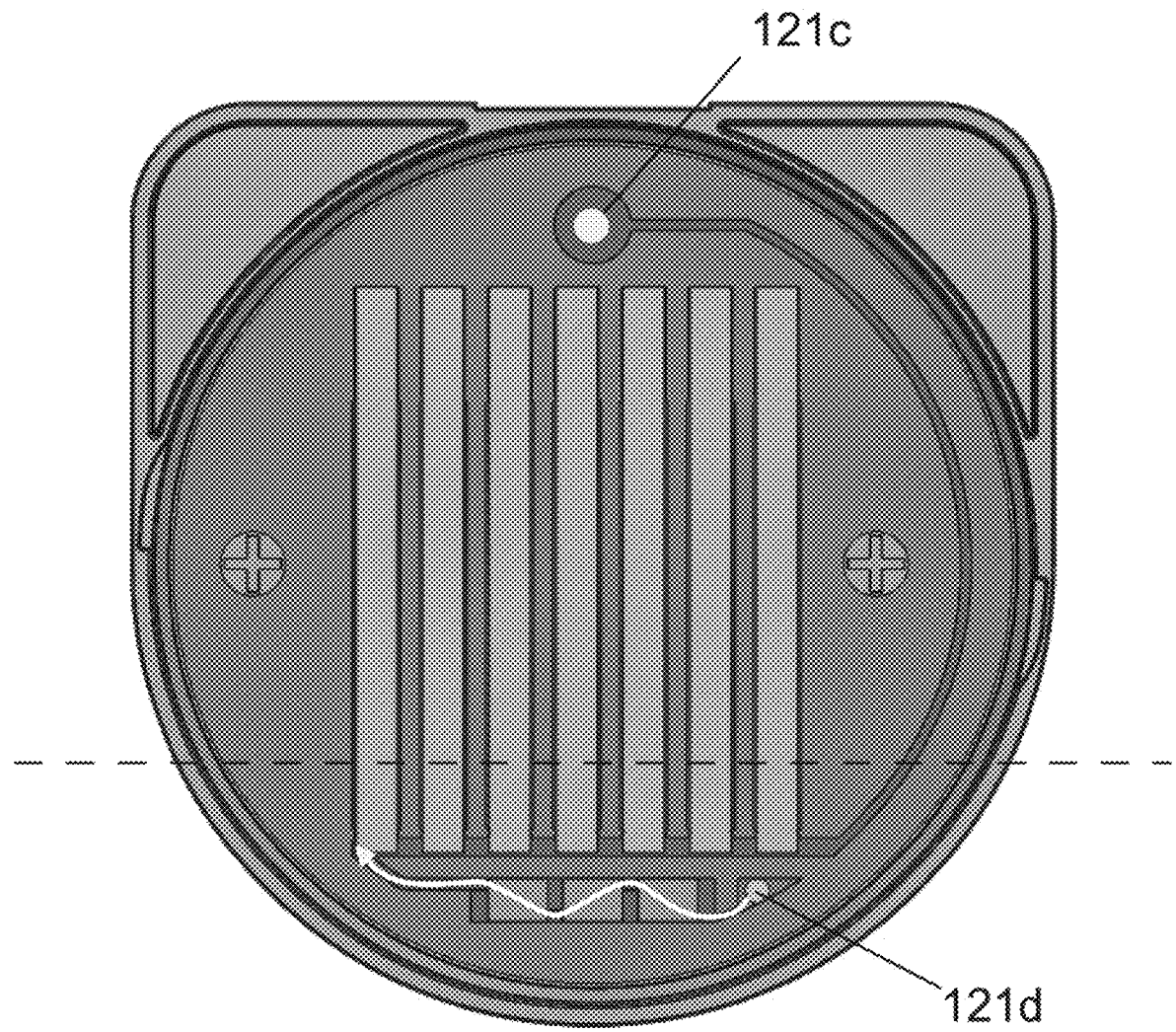
FIG. 13 is a drawing of an assay device lid showing the assay device lid body vent hole 121c and the assay device lid body inlet hole 121d. In the embodiment of the assay device lid shown in FIG. 13, sample (white arrow) flows through the assay device lid body inlet hole 121d and contacts the adulterant test strips. The dotted line shows the maximum liquid height when a sample has been introduced into the device according to embodiments of the technology described herein.
Figure 14:
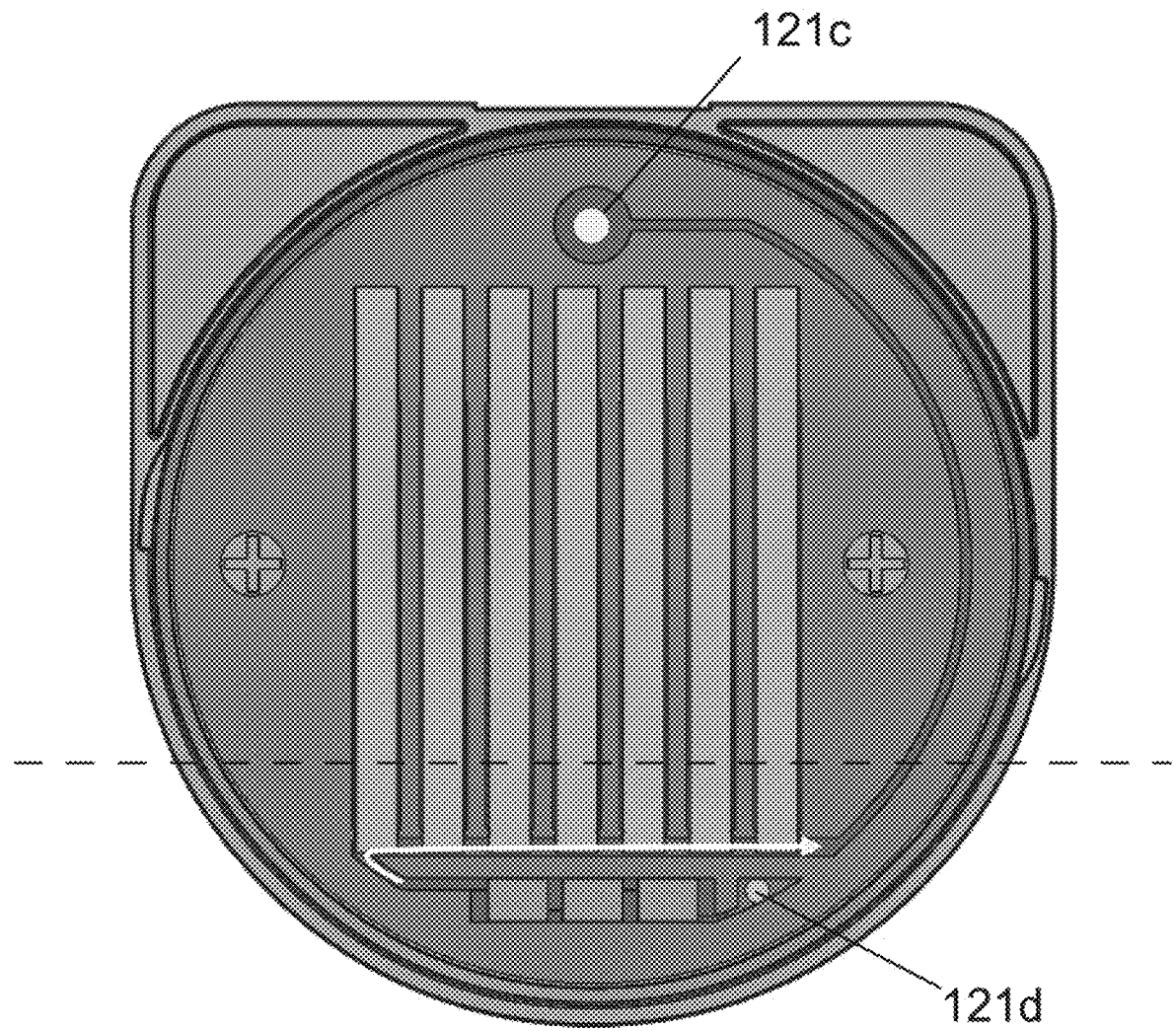
FIG. 14 is a drawing of an assay device lid showing the assay device lid body vent hole 121c and the assay device lid body inlet hole 121d. In the embodiment of the assay device lid shown in FIG. 14, sample (white arrow) has flowed pass the adulterant test strips and contacts the test strips. The dotted line shows the maximum liquid height when a sample has been introduced into the device according to embodiments of the technology described herein. In some embodiments, the liquid flows in a controlled manner sequentially along the bottom of the test strips toward the assay device lid body vent hole 121c. The liquid movement helps to push trapped air in the channel through the vent, which prevents formation of air bubbles in the channel that can prevent test strips from running correctly.

In particular, the assay device lid 120 comprises an assay device lid body 121 and an assay device lid label 122 (see, e.g., FIG. 3, FIG. 5A, and FIG. 5B). The assay device lid body comprises an assay device lid body channel 121a, assay device lid body test strip receptacles 121b (e.g., configured to accept one or more test strips 124a), an assay device lid body vent hole 121c, and an assay device lid body inlet hole 121d (see, e.g., FIG. 7, FIG. 8, and FIG. 12). The assay device lid label 122 comprises a laser target 122a (e.g., sealing the assay device lid body vent hole 121c when the assay device lid body vent hole is in a closed state to provide an airlock), a test strip viewing window 122b, an adulterant test strip viewing window 122c, a barcode 122d, and an assay device lid tab 122e (see, e.g., FIG. 3, FIG. 4A, and FIG. 4B). The assay device lid 120 further comprises an assay device lid gasket 123 comprising an assay device lid gasket inlet hole 123a, an assay device test strip panel 124 comprising one or more assay device test strips 124a, and one or more assay device adulterant test strips 125 (see, e.g., FIG. 4A, FIG. 5A, FIG. 5B, FIG. 8, and FIG. 9). Embodiments provide that the assay device lid gasket 123 is compressed between the assay device lid 120 and assay device cup when the assay device lid is engaged with the assay device cup, e.g., to seal a sample inside the cup (see, e.g., FIG. 10). In this configuration, the gasket improves the seal between the lid and the cup to securely hold the sample inside the cup. In some embodiments, the technology comprises use of one (e.g., a single) gasket (e.g., foam gasket) that both seals the test strips into the lid and seals the lid onto the cup.

The reader apparatus 200 is configured to automatically read the visual indications (e.g., lines) produced by the test strips in the assay device 100 to generate data signals representative thereof. The reader apparatus comprises an assay device receiver 202 for receiving the assay device therein in a particular orientation. More particularly, the assay device receiver comprises surfaces intended to mate with surfaces on the assay device, e.g., a D-shaped lid that complements a D-shaped assay device receiver to compel the assay device to a particular orientation upon insertion into the reader apparatus. This orientation places the aforementioned lid windows within the field of view of a camera carried by the reader apparatus.

Figure 6A:
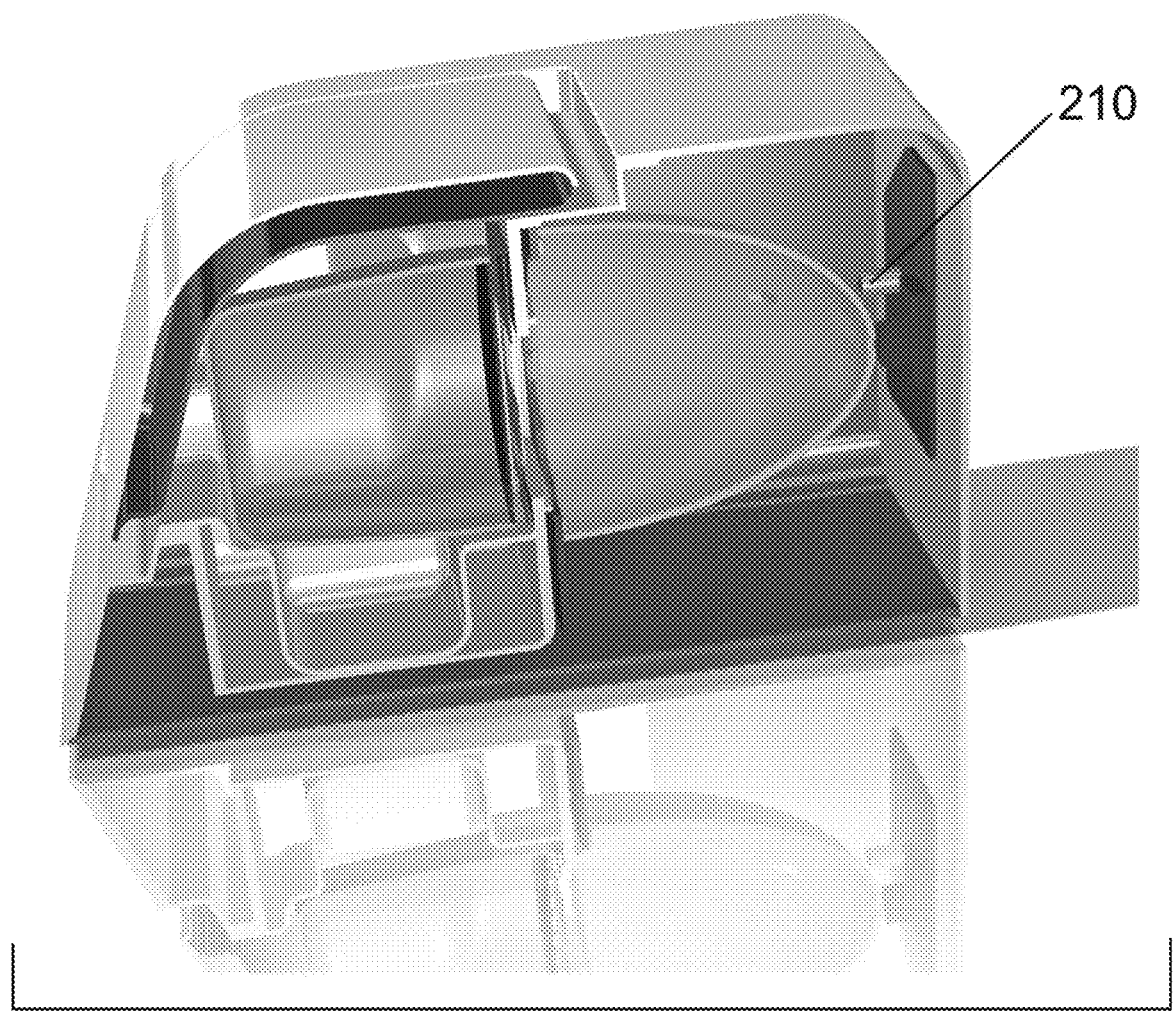
FIG. 6A is a drawing of a reader apparatus 200. The reader apparatus 200 comprises a laser source 210.
Figure 6B:
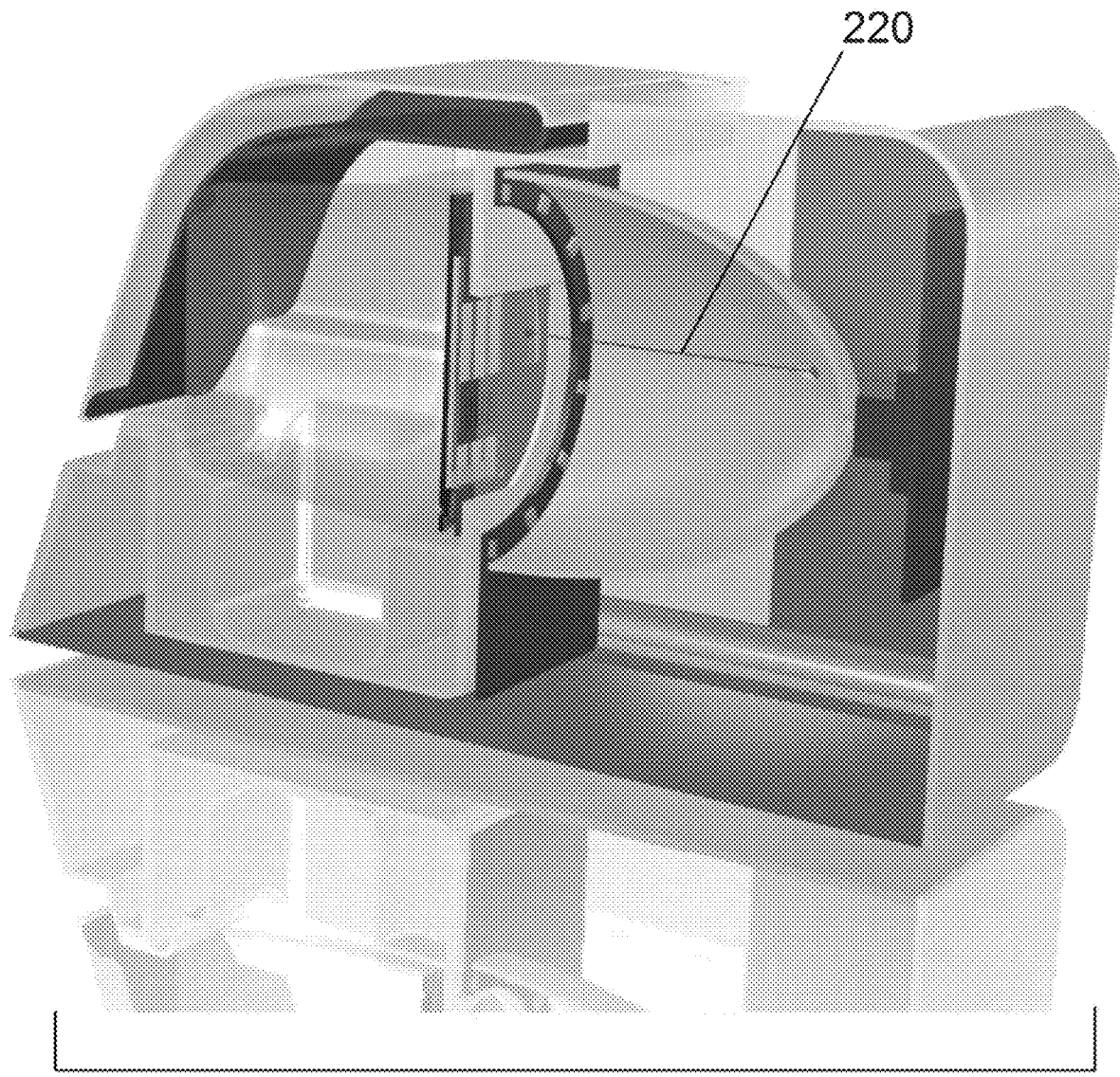
FIG. 6B is a drawing of a reader apparatus 200. The laser light source of the reader apparatus 200 has been activated to produce a laser 220.

Further, the reader apparatus 200 comprises a label 201 to guide assay device alignment (e.g., upon insertion of the assay device 100 into the reader apparatus 200), a receiver 202 configured to accommodate the assay device (e.g., a D-shaped assay device receiver), a reader apparatus laser source 210 (e.g., that produces a laser 220 upon actuation) (see, e.g., FIGS. 6A and 6B), a reader apparatus lid 230 comprising a relief 231 to aid a user in opening a lid, and a removable reservoir 240 to contain leaks (e.g., comprising space 241 on its sides for fingers to access and grip the device cup) (see, e.g., FIG. 1A, FIG. 1B, FIG. 1C, and FIG. 1D). In some embodiments, the reader apparatus comprises a START switch and/or a display panel.

In some embodiments, the assay device cup, the assay device lid body channel, assay device lid body vent hole, and assay device lid body inlet hole are designed and/or configured to allow a proper amount of sample (e.g., a metered amount) from the assay device cup into the assay device lid body channel to contact the test strips. For example, in some embodiments, the volume and/or dimensions of the assay device cup is/are designed and/or configured to allow a proper amount of sample (e.g., a metered amount) to move from the assay device cup into the assay device lid body channel to contact the test strips, e.g., when a typical fluid specimen (e.g., a urine sample of approximately 1 ml to 100 ml, 10 to 500 ml, and/or up to 1 or more liters) is present in the assay device cup and the assay device cup is placed on its side so that the fluid specimen contacts the assay device lid (e.g., oriented with the axis of the cup essentially parallel with the earth), e.g., when placed into a reader apparatus (e.g., as shown in FIG. 1A) and the assay device lid body vent hole is provided in an open state to release an airlock.

The device lid body channel shape, width, length, pattern, path, etc. are designed and/or configured so that puncturing, poking, tearing, or otherwise disrupting the assay device lid label and providing the assay device lid body vent hole in an open state releases an airlock and atmospheric pressure causes a proper amount (e.g., a metered amount) of sample (e.g., a metered amount) from the assay device cup to flow into the assay device lid body channel to contact the test strips. In some embodiments, the channel width is approximately 1-10 mm (e.g., 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 mm) In some embodiments, the channel varies in width along its length. In some embodiments, the channel directs flow of the fluid specimen to contact one or more assay device adulterant test elements and/or one or more assay device test strips. In some embodiments, the channel comprises a first portion comprising a metered amount of the fluid specimen and a second portion comprising air.

In some embodiments, the channel path is straight, curved, S-shaped, C-shaped, and/or comprises one or more turns. Accordingly, the volume and dimensions of the cup and the distance between the assay device lid body vent hole and the assay device lid body inlet hole is/are designed and/or configured to provide an appropriate static head pressure at approximately sea level to push an amount of sample into the assay device lid body channel to contact the test strips without flooding the test strips (e.g., when the assay device vent hole is provided in an open state). In some embodiments, the channel shape, width, length, pattern, and/or path minimize capillary flow of the fluid specimen, e.g., such that movement of the fluid specimen is controlled by the volume and design of the assay device cup, assay device lid body channel, assay device lid body vent hole, and assay device lid body inlet hole; and by the open or closed state of the assay device lid body vent hole (e.g., by the state of the label covering the assay device lid body vent hole).

Figure 2A:
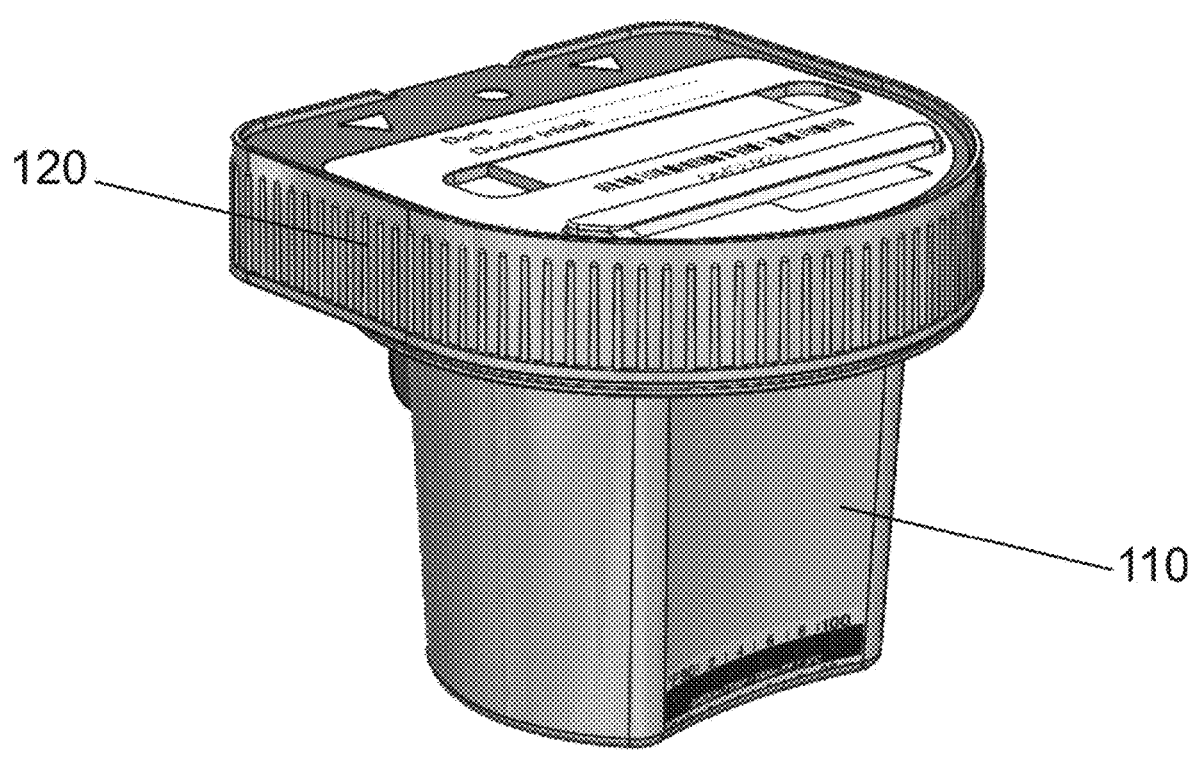
FIG. 2A is a drawing of an assay device 100 comprising an assay device cup 110 and an assay device lid 120. In the embodiment of the assay device lid 120 shown in FIG. 2A, the assay device lid 120 has a "D" shape, e.g., the assay device lid 120 comprises a rounded portion and a flat portion.
Figure 2B:
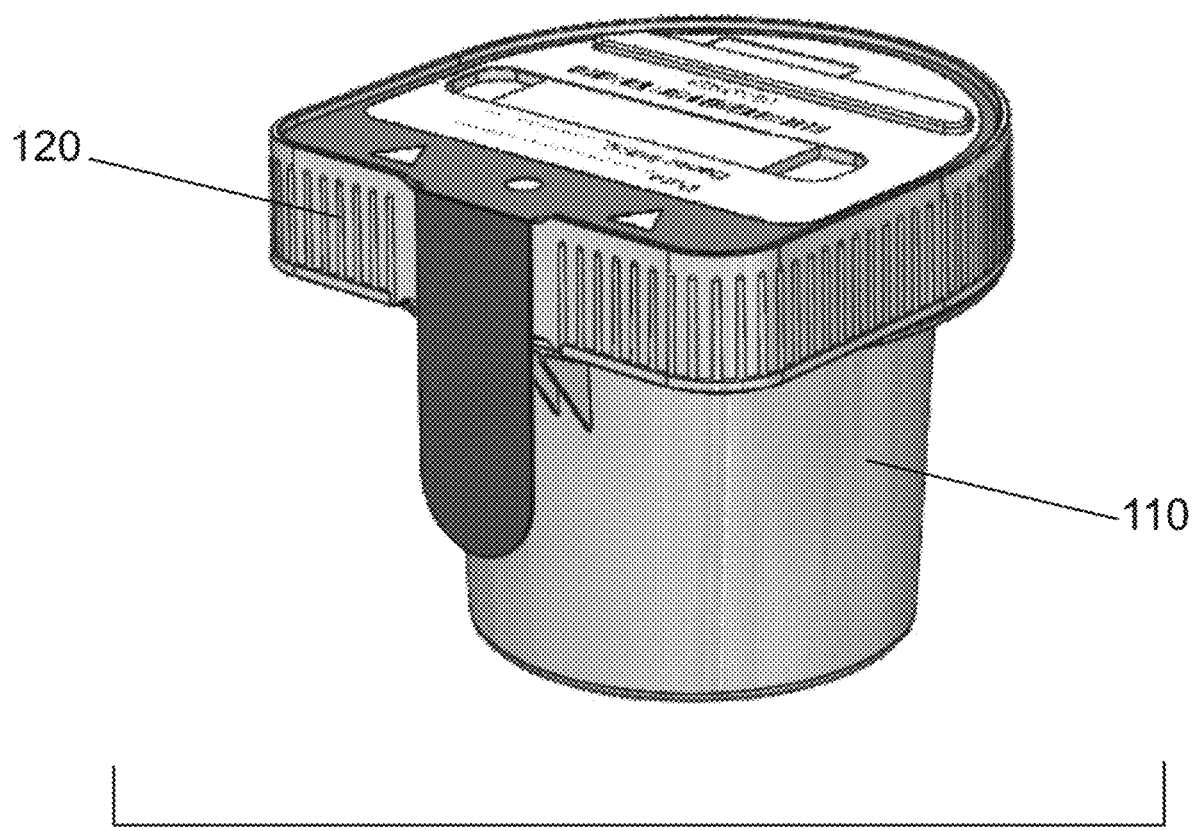
FIG. 2B is a drawing of an assay device 100 comprising an assay device cup 110 and an assay device lid 120. In the embodiment of the assay device lid 120 shown in FIG. 2B, the assay device lid 120 has a "D" shape, e.g., the assay device lid 120 comprises a rounded portion and a flat portion.

In some embodiments, one of ordinary skill in the art, e.g., (fluid mechanics) can design an assay device cup and assay device lid comprising an assay device lid body channel, assay device lid body vent hole, and assay device lid body inlet hole to provide an appropriate head pressure for a typical fluid specimen (e.g., a urine sample of approximately 1 ml to 100 ml, 10 to 500 ml, and/or up to 1 or more liters) that is present in the assay device cup when the assay device cup is placed on its side so that an appropriate amount (e.g., a metered amount) of the fluid specimen flows from the assay device cup into the assay device lid body channel to contact the test strips, e.g., when placed into a reader apparatus (e.g., as shown in FIG. 1A) and the assay device lid body vent hole is provided in an open state to release an airlock. In some embodiments, the distance from the top of the fluid specimen to the assay device lid body inlet hole is approximately 1-5 cm (e.g., 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 cm) when the device cup is placed on its side so that the fluid specimen contacts the assay device lid (e.g., oriented with the axis of the cup essentially parallel with the earth), e.g., when placed into a reader apparatus (e.g., as shown in FIG. 1A). In some embodiments, prior to providing the lid body vent hole in an open state, the height of the fluid specimen in the assay device cup has a first height (e.g., approximately 1-5 cm (e.g., 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 cm)) when the assay device cup is placed on its side so that the fluid specimen contacts the assay device lid (e.g., oriented with the axis of the cup essentially parallel with the earth), e.g., when placed into a reader apparatus (e.g., as shown in FIG. 1A). In some embodiments, after the lid body vent hole is provided in an open state, the height of the fluid specimen in the assay device cup has a second height ((e.g., approximately 1-5 cm (e.g., 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 cm)) that is less than the first height of the fluid specimen in the assay device cup. And, in some embodiments, after the lid body vent hole is provided in an open state, the fluid specimen has a third height in the assay device lid body that is the same and/or essentially the same as the second height of the fluid specimen in the assay device cup (e.g., the height of the fluid specimen in the assay device lid body and the height of the fluid specimen in the assay device lid are substantially the same).

In some embodiments, one of ordinary skill in the art can determine the static head pressure according to:

$$\psi = \frac{p}{\gamma} = \frac{p}{\rho g}$$

where $\Psi$ is the static pressure head, p is the fluid pressure, $\Upsilon$ is the specific weight of the fluid specimen (e.g., approximately 9.5-10.0 kN/m$^3$ for a urine sample at room temperature (e.g., approximately 20 C) to body temperature (e.g., approximately 40 C)), $\rho$ is the density of the fluid (e.g., approximately 1.01 to 1.1 g/ml for urine), and g is the acceleration of gravity.

Embodiments provide that the assay device (e.g., the cup and lid) is manufactured using traditional manufacturing techniques known in the mechanical and manufacturing arts and provide that the assay device is constructed from various materials. These materials can include metal, silicon, glass, ceramic, plastic, and synthetic and natural polymers or any combination thereof. In some embodiments of the technology, the assay device is manufactured from a polypropylene composite using an appropriate manufacturing method. In some embodiments, the assay device is constructed from polystyrene (e.g., high impact polystyrene) using similar methods known in the art of plastics construction. Methods of manufacturing can include but are not limited to milling, casting, blowing, spinning, injection molding, machining, and three-dimensional printing. In some embodiments of the present technology, the assay device is substantially transparent so that a user can observe a sample in the cup interior by observation of the outside surface of the assay device. In some embodiments, the cup is constructed separately from the lid and the cup and lid may be produced from the same or different materials.

The size of the assay device (e.g., cup) is appropriate to meet or exceed the expected volumetric size of the sample to be contained and/or held within the chamber. As a lower limit, embodiments provide that the cup volume is sufficiently large to transfer an adequate volume of a sample to the test strips for assay, considering adhesive forces between the materials of construction and the sample that reduce transfer of the sample to the test strips. As an upper limit, embodiments provide that the cup volume is sufficiently small to prevent the sample from overloading the cup (and, consequently, the test strips) due to forces exerted from a sample entering the assay device lid body channel when the cup is full. In exemplary embodiments, the cup comprises a size to accommodate sample volumes greater than approximately 1.0 milliliter, 0.1 milliliter, 0.01 milliliter, 0.001 milliliter, or approximately 0.0001 milliliter and is manufactured to accommodate volumes less than approximately 1 milliliter, 5 milliliters, 10 milliliters, 50 milliliters, 100 milliliters, 250 milliliters, 500 milliliters, 750 milliliters, 1,000 milliliters, or approximately 2,000 milliliters.

Systems

These various components of the assay device and their functions provide embodiments systems for testing a sample for the presence, absence, and/or concentration of an analyte. For example, in some embodiments, systems comprise a reader apparatus 200 comprising a reader apparatus lid 230 that can be moved between an open state and a closed state (see, e.g., FIG. 1A and FIG. 1B). When the reader apparatus lid is in the open state, the reader apparatus may accept an assay device 100 (e.g., in an assay device receiver 202). In some embodiments, the assay device is D-shaped and the reader apparatus is configured to accept the assay device in a D-shaped assay device receiver 202 (see, e.g., FIG. 1A and FIG. 1C).

Figure 1C:
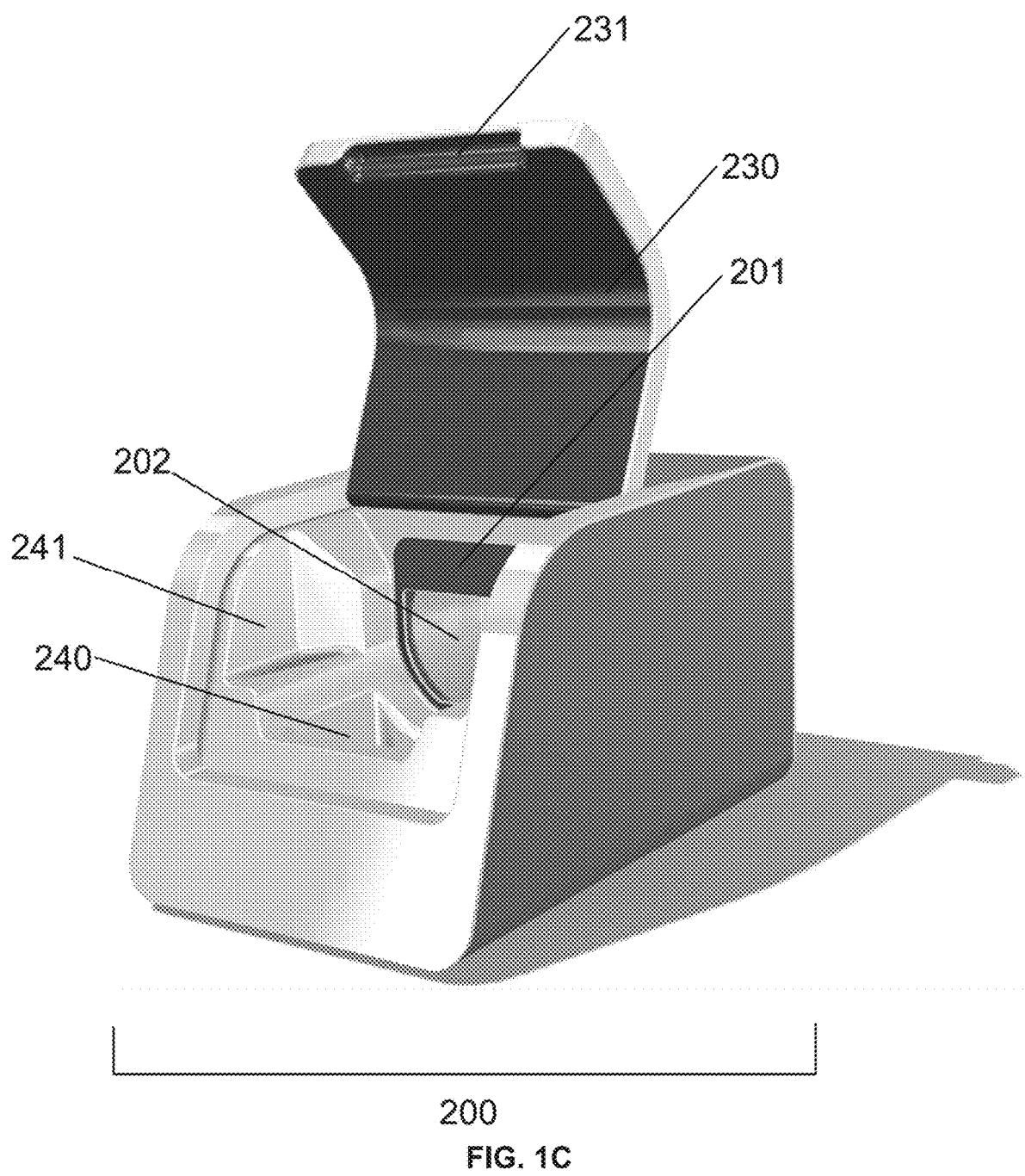
FIG. 1C is a drawing of a reader apparatus 200. The reader apparatus comprises a reader apparatus lid 230 in an open state. The reader apparatus lid 230 comprises a reader apparatus lid relief, e.g., to aid a user in opening the reader apparatus lid 230. The reader apparatus 200 comprises a reader apparatus label 201, e.g., to guide a user in inserting an assay device into the reader apparatus 200. The reader apparatus 200 comprises an assay device receiver 202 (e.g., a D-shaped assay device receiver). The reader apparatus 200 comprises a reservoir 240, e.g., to contain leaks. The reservoir 240 comprises space 241 on its sides, e.g., to allow the fingers of a user to grip the assay device.
Figure 1D:
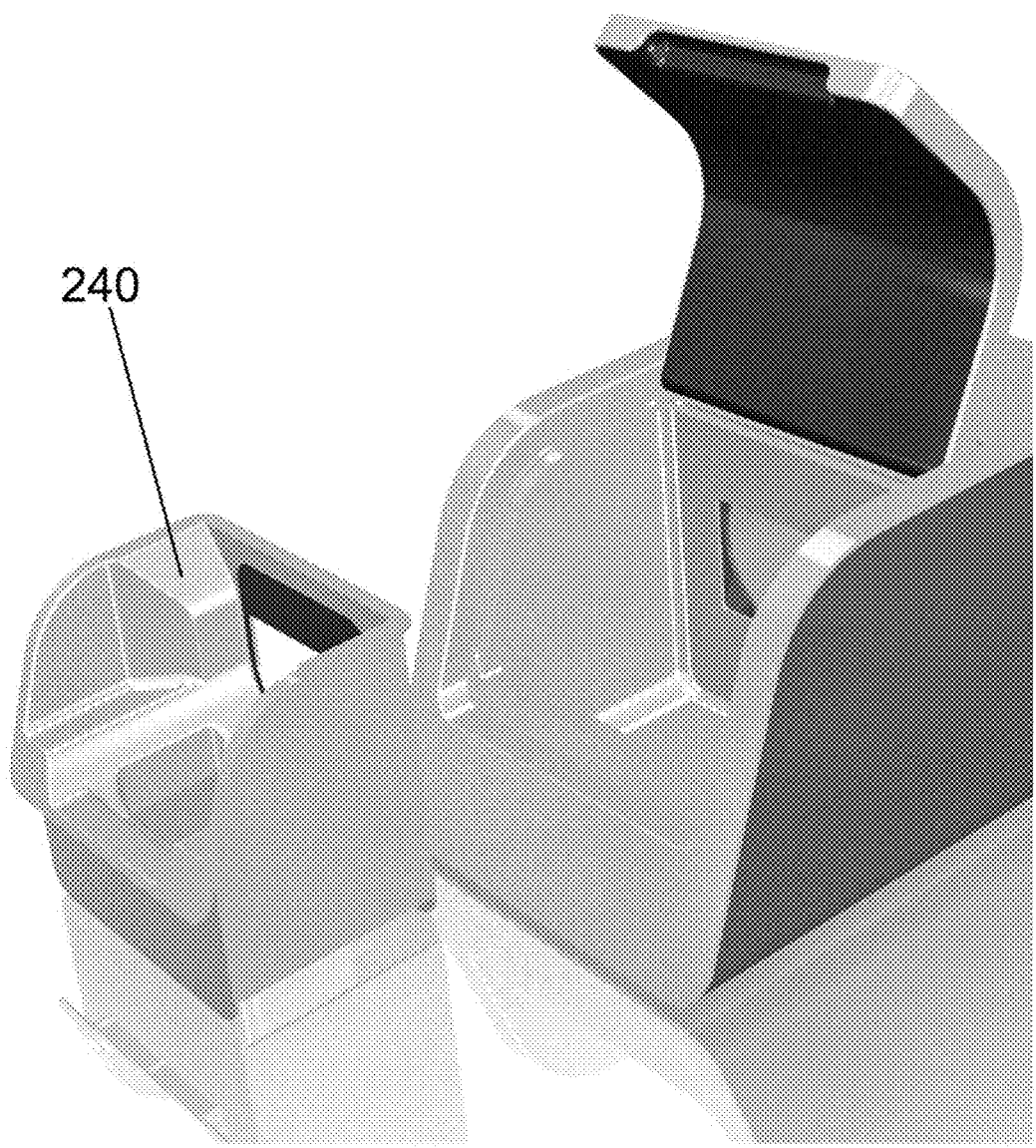
FIG. 1D is a drawing of a reservoir 240 that is a removable reservoir and that is removed from a reader apparatus.

In some embodiments, the reader apparatus lid 230 comprises a reader apparatus lid relief 231, e.g., to aid a user in opening the reader apparatus lid 230 (see, e.g., FIG. 1C). In some embodiments, the reader apparatus 200 comprises a reader apparatus label 201, e.g., to guide a user in inserting an assay device into the reader apparatus 200 (see, e.g., FIG. 1C), e.g., into the assay device receiver (e.g., a D-shaped assay device receiver) 202. In some embodiments, the reader apparatus 200 comprises a reservoir 240 (e.g., a removable reservoir) (see, e.g., FIG. 1C), e.g., to contain leaks. The removable reservoir 240 may be removed to dispose of leaks and to clean the removable reservoir 240 (see, e.g., FIG. 1D). In some embodiments, the reservoir 240 comprises one or more spaces 241 (e.g., along its sides) (see, e.g., FIG. 1C), e.g., to allow the fingers of a user to grip the assay device when inserting the assay device into the reader apparatus and/or removing the assay device from the reader apparatus.

In some embodiments, the technology provides systems comprising a reader apparatus 200 and an assay device 100. In some embodiments, the assay device 100 comprises an assay device cup 110 and an assay device lid 120 (see, e.g., FIG. 2A and FIG. 2B). In some embodiments, the assay device (e.g., the assay device lid 120) has a "D" shape. As used herein, the terms "D-shape" and "D-shaped" refer to a shape comprising a rounded portion and a flat portion (e.g., similar to the roman alphabet letter "D").

In some embodiments, the assay device lid 120 comprises an assay device lid label 122 (see, e.g., FIG. 3). In some embodiments, the assay device lid label 122 comprises an assay device lid label laser target 122a (see, e.g., FIG. 3 and FIG. 4B). The assay device lid label laser target provides a seal for the assay device lid body vent hole 121c. That is, when the assay device lid label laser target (e.g., seal) is intact (e.g., not broken, disrupted, pierced, etc.), the assay device lid body vent hole 121c is in a closed state and provides an airlock for the assay device lid body channel 121a. When the assay device lid body channel 121a is in the closed ("airlocked") state, sample does not flow from the assay device cup to wet the test strips. The assay device lid label laser target (e.g., seal) may be broken (e.g., disrupted, pierced, etc.) to provide the assay device lid body vent hole 121c in an open state, e.g., by a laser 220, to release the airlock as further described herein. While embodiments of the system are described using a laser to release the airlock, it should be understood that mechanical (e.g., piercing with a pin) or other mechanisms (e.g., electrical, chemical, etc.) of puncturing a seal to release the airlock may also be employed.

In some embodiments, the assay device lid 120 comprises an assay device lid label test strip viewing window 122b (see, e.g., FIG. 3). The assay device lid label test strip viewing window 122b is cut out of the assay device lid and/or is optically clear or translucent to provide optical viewing of the test strips (e.g., by an eye and/or by an imaging component (e.g., a camera)). In some embodiments, the assay device lid 120 comprises an assay device lid label adulterant viewing window 122c (see, e.g., FIG. 3). The assay device lid label adulterant viewing window 122c is cut out of the assay device lid and/or is optically clear or translucent to provide optical viewing of the assay device adulterant test strips (e.g., by an eye and/or by an imaging component (e.g., a camera). In some embodiments, the assay device lid 120 comprises an assay device lid label barcode 122d (see, e.g., FIG. 3). In some embodiments, the barcode comprises one or more parts, e.g., to convey one or more types of information (e.g., assay type, lot number, etc.) In some embodiments, the assay device lid 120 comprises one or more fiducial marks for alignment and/or registration of an image recorded of the assay device lid. The windows device lid label test strip viewing window 122b, assay device lid label adulterant viewing window 122c, lid label barcode 122d, and optional fiducial marks are arranged to provide an image field suitable for recording by a camera (e.g., suitable for being imaged onto the focal plane of camera). In an exemplary embodiment, the image field has width and height dimensions, respectively, that are approximately 1446 mils and 1084 mils. In said exemplary embodiment, the image field is imaged onto a camera view field having 640 pixels horizontally and 480 pixels vertically.

In some embodiments, the assay device lid 120 comprises an assay device lid tab 122e (see, e.g., FIG. 3, FIG. 4A, and FIG. 4B). In some embodiments, the assay device lid tab 122e comprises an adhesive for adhering a portion of the assay device lid tab 122e to the assay device cup 110 to provide a tamper evident seal (e.g., when the assay device comprises a sample and the assay device lid 120 is engaged with the assay device cup).

In some embodiments, the assay device lid 120 comprises an assay device lid gasket 123 (see, e.g., FIG. 4A and FIG. 5A). The assay device lid gasket 123 comprises an assay device lid gasket inlet hole 123a (see, e.g., FIG. 4A and FIG. 5A). In some embodiments, engaging the assay device lid 120 with the assay device cup 110 (e.g., by engaging threads of the assay device lid 120 with threads of the assay device cup 110 (e.g., by screwing the assay device lid 120 onto the assay device cup 110)) compresses the assay device lid gasket 123 between the assay device lid 120 and the assay device cup 110 (see, e.g., FIG. 10). In some embodiments, the technology comprises use of one (e.g., a single) gasket (e.g., foam gasket) that both seals the test strips into the lid and seals the lid onto the cup.

In some embodiments, the assay device lid 120 comprises an assay device test strip panel 124 (see, e.g., FIG. 5A and FIG. 5B). The assay device strip panel 124 is configured to accept and retain one or more assay device test strips 124a (see, e.g., FIG. 8). Test strips are known in the art. See, e.g., U.S. Pat. Nos. 4,366,241; 4,094,647; 4,235,601; 4,361,537; 5,120,643; 6,841,159; 6,352,862; 5,622,871; 5,798,273; 5,160,701; 5,141,850; 5,451,504; 5,415,994; 5,559,041; 5,569,608; 5,837,546; and 7,344,893, each of which is incorporated herein by reference. See also Int'l Pat. App. Nos. WO 91/12336 and 88/08534, and European Patent Nos.

EP 0 505 636 and EP 0 284 232, each of which is incorporated herein by reference. See also Bangs Laboratories TechNote 303 "Lateral Flow Tests" (20 Mar. 2013); Posthuma-Trumpie (2009) "Lateral flow (immuno) assay: its strengths, weaknesses, opportunities, and threats. A literature review" Anal Bioanal Chem 393: 569-82; and Qian and Bau (2003) "Analysis of lateral flow biodetectors: competitive format" Departmental Papers (MEAM). 123, each of which is incorporated herein by reference.

In some embodiments, the reader apparatus 200 comprises a puncturing means, e.g., to puncture the assay device lid label sealing the assay device lid body vent hole 121c. Puncturing, poking, tearing, or otherwise disrupting the assay device lid label sealing the assay device lid body vent hole 121c provides the assay device lid body vent hole 121c in an open state. Providing the assay device lid body vent hole 121c in an open state releases an airlock. Releasing the airlock allows a metered aliquot of a sample to flow from the assay device cup to wet one or more assay device test strips (e.g., by flowing through the assay device lid body channel 121a). In some embodiments, the puncturing means is a laser source 210 that produces a laser 220 (see, e.g., FIG. 6A and FIG. 6B). In some embodiments, the assay device lid label comprises an assay device lid label laser target 122a (see, e.g., FIG. 3 and FIG. 4B) that seals the assay device lid body vent hole 121c (see, e.g., FIG. 7). Accordingly, in some embodiments, puncturing, poking, tearing, or otherwise disrupting the assay device lid label laser target 122a sealing the assay device lid body vent hole 121c provides the assay device lid body vent hole 121c in an open state. Providing the assay device lid body vent hole 121c in an open state releases an airlock. Releasing the airlock allows a metered aliquot of a sample to flow from the assay device cup to wet one or more assay device test strips (e.g., by flowing through the assay device lid body inlet hole 121d and assay device lid body channel 121a). While embodiments discussed herein relate to a puncturing means that is a laser, embodiments comprise other forms of a puncturing means that are capable of opening the vent hole including, but not limited to, a pin, a knife, heat, electricity, a screw, high pressure, a piston, a solvent, etc.

The assay device lid body comprises channels, one or more receptacles for test strips, and a vent hole (see, e.g., FIG. 7 and FIG. 8) that may be provided in a closed state or in an open state (e.g., depending on the integrity of the assay device lid label covering (e.g., sealing) the vent hole. In some embodiments, the assay device lid body comprises an assay device lid body channel 121a, an assay device lid body test strip receptacle 121b (e.g., a plurality of lid body test strip receptacles), and an assay device lid body vent hole 121c (see, e.g., FIG. 7 and FIG. 8). The one or more assay device test strip receptacles is/are configured to receive one or more assay device test strips 124a (see, e.g., FIG. 8). In some embodiments, the assay device lid body comprises an assay device adulterant test strip 125 (e.g., a plurality of assay device adulterant test strips) (see, e.g., FIG. 8).

Figure 9:
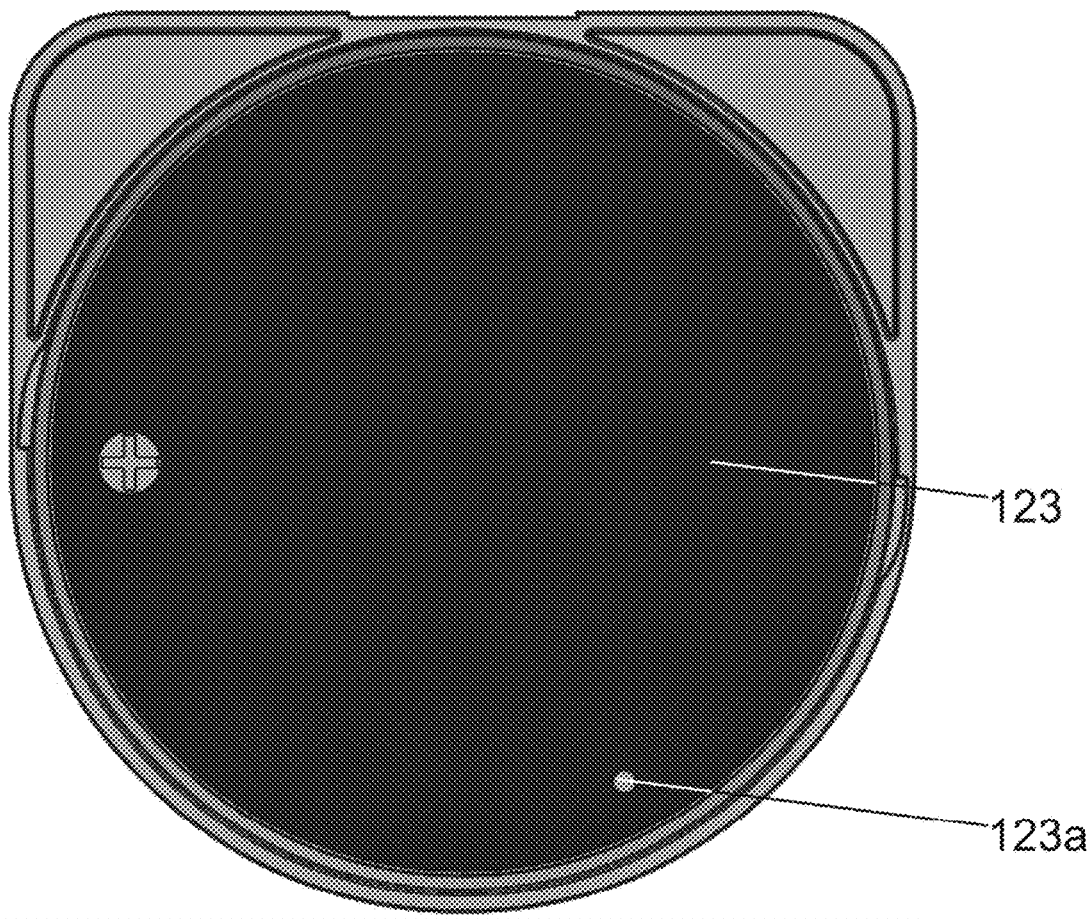

In some embodiments, the assay device lid 120 comprises an assay device lid gasket 123 comprising an assay device lid gasket inlet hole 123a (see, e.g., FIG. 9). When the assay device lid body vent hole 121c is in an open state (e.g., to release the airlock), the assay device lid body channel is open and sample flows from the assay device cup through the assay device lid gasket inlet hole 123a (and through the assay device lid body inlet hole 121d) to wet the test strips and, optionally, the adulterant test strips (see, e.g., FIG. 12, FIG. 13, FIG. 14, and FIG. 15). The assay device lid 120 is designed (e.g., the assay device lid body channel 121a, assay device lid body vent hole 121c, and assay device lid body inlet hole 121d are designed) such that a metered amount of sample is provided to the test strips. For example, the dimensions of the interior volumes (e.g., channel 121a) are selected to permit only the metered amount of sample to contact the test strips. In some embodiments, the metered amount of sample is a volume of 1-1000 μl (e.g., 1, 2, 3, 4, 5, 6, 7, 8, 9, 10, 20, 30, 40, 50, 60, 70, 80, 90, 100, 200, 300, 400, 500, 600, 700, 800, 900, or 1000 μl) or 1-100 ml (e.g., 1, 2, 3, 4, 5, 6, 7, 8, 9, 10, 20, 30, 40, 50, 60, 70, 80, 90, or 100 ml).

Figure 15:
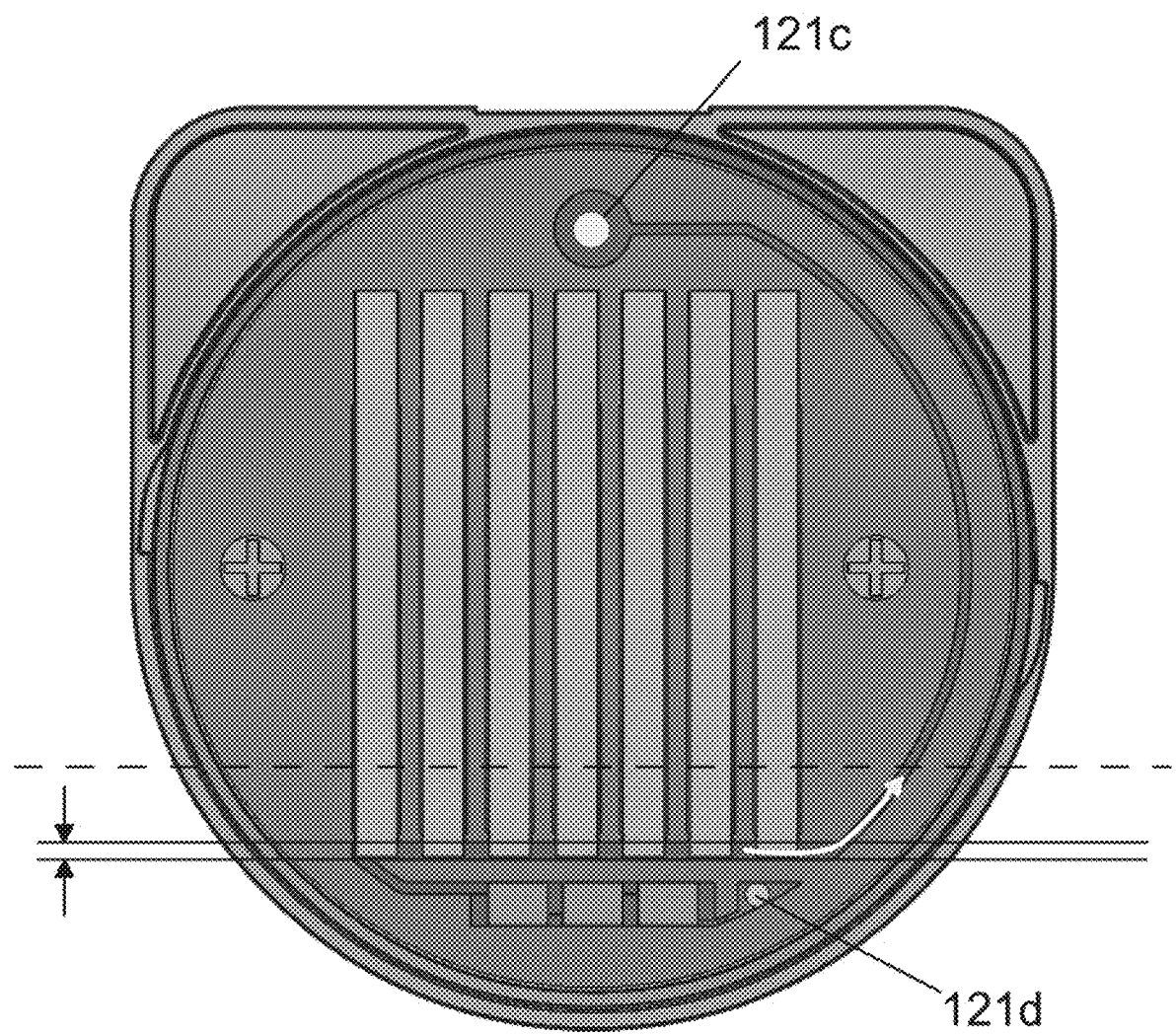
FIG. 15 is a drawing of an assay device lid showing the assay device lid body vent hole 121c and the assay device lid body inlet hole 121d. In the embodiment of the assay device lid shown in FIG. 13, sample (white arrow) has flowed pass the test strips. The dotted line shows the maximum liquid height when a sample has been introduced into the device according to embodiments of the technology described herein. The regions of the test strips between the solid lines are contacted by the sample and the test strips are not flooded with sample. The regions above the solid lines are not contacted directly by the sample; sample flows from the bottom of the test strips into the test strips by capillary action.

In particular, liquid flowing through the assay device lid gasket inlet hole 123a and assay device lid body inlet hole 121d into the assay device lid body channel 121a only wets the bottom portion of the test strips and does not flood the test strips (see, e.g., FIG. 15). In some embodiments, the bottom 0.5 to 10% (e.g., 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0%) of the test strips are wetted by the metered amount of sample. In some embodiments, the bottom 0.1 to 2.0 mm (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mm) of the test strips are wetted by the metered amount of sample.

Some guidance related to the construction and use of an assay device comprising a test strip in a lid for testing a urine sample and a reader device for imaging a test result and analyzing the image data is provided in, e.g., U.S. Pat. Nos. 7,537,733 and 6,342,183, each of which is incorporated herein by reference. U.S. Pat. No. 7,537,733, incorporated herein by reference, provides technologies for acquiring an image of a test strip by a reader and analyzing image data to detect the presence (or absence) of a line on a test strip and provide a test result to a user or to communicate over a network.

Some embodiments of the technology provided herein further comprise functionalities for collecting, storing, and/or analyzing data. For example, in some embodiments the systems described herein comprise a processor, a memory, and/or a database for, e.g., storing and executing instructions, analyzing data, performing calculations using the data, transforming the data, and storing the data. Moreover, in some embodiments a processor is configured to control the reader apparatus (e.g., laser source, camera). In some embodiments, the processor is used to initiate and/or terminate measurement and data collection. In some embodiments, the device comprises a user interface (e.g., a keyboard, buttons, dials, switches, and the like) for receiving user input that is used by the processor to direct a measurement. In some embodiments, the device further comprises a data output for transmitting data to an external destination, e.g., a computer, a display, a network, and/or an external storage medium.

Methods

In some embodiments, the technology relates to methods for testing a sample for the presence, absence, and/or concentration of an analyte. In some embodiments, methods comprise obtaining, producing, or providing a sample. In some embodiments, methods comprise providing a sample into an assay device cup of an assay device as described herein. For example, embodiments relate to a sample donor at a local site providing a fluid sample (e.g., urine) into the cup, e.g., the sample donor voids into the cup. In some embodiments, methods comprise engaging an assay device lid to the assay device cup. In some embodiments, methods comprise compressing a gasket of the assay device lid to seal the sample in the assay device cup. In some embodiments, a site administrator records identification information relating to the sample or to the individual who produced the sample and secures the lid to the cup in a tamper evident fashion (e.g., by adhering an assay device lid tab 122e to the assay device cup).

In some embodiments, a user and/or administrator enters identification information relating to the sample or to the individual who produced the sample into the reader apparatus. For example, in some embodiments, a site administrator enters donor and client (e.g., employer) information (e.g., using an input device) into a database stored either in a processor of the reader apparatus or a remote host computer. In some embodiments, the administrator and donor initial the adhered assay device lid tab and review a chain of custody document. In some embodiments, the donor and administrator both apply their signatures to a signature pad and a copy of the chain of custody document is printed and given to the donor.

In some embodiments, the sealed assay device is inserted into a reader apparatus as described herein. For instance, in some embodiments, a user and/or administrator places the assay device into the receptacle (e.g., D-shaped receptacle) of the reader apparatus. In some embodiments, the user and/or administrator closes the lid of the reader apparatus.

In some embodiments, an operational sequence is initiated to assay the sample in the assay device cup. In some embodiments, the operational sequence is initiated by a local user and/or administrator. In some embodiments, the reader apparatus alerts a remote host computer that an assay device has been inserted into the reader apparatus and the operational sequence is initiated by the remote host computer. The operational sequence is automatically executed under the control of a programmed microprocessor of the reader apparatus.

In some embodiments, the operational sequence for assaying a sample comprises a series of assay steps. For example, in some embodiments, a camera captures an image of the assay device lid and a processor verifies acceptability to proceed. For example, in some embodiments, an initial image is captured by the camera to examine the barcode and other lid features to determine if it is valid. If the barcode is not valid, this fact is displayed to the site administrator for further action. An invalid barcode can indicate that the assay device is inserted incorrectly, that no cup has been inserted, or that a fake cup has been inserted. If the administrator cannot resolve the issue and the barcode is indeed invalid, testing is aborted and the sealed cup is sent for laboratory analysis.

In some embodiments, the processor actuates a piercing means (e.g., actuates a laser source to produce a laser) to open a vent hole in the assay device lid and thus allows a metered amount of the sample to wet the analyte test strips and, optionally, the adulteration test strips. The design of the assay device lid (e.g., vents and channels) prevents the sample from rising above a specified height determined by the design of the assay device lid (see, e.g., FIG. 11-15, dotted line). When the assay device lid body vent hole is in an open state (e.g., as a result of the piercing means (e.g., laser)) (see, e.g., FIG. 12), an airlock is released and sample flows from the assay device cup through the assay device lid gasket inlet hole and the assay device lid body inlet hole into the assay device lid body channel. Sample flows through the assay device lid body inlet hole (see, e.g., FIG. 13, white arrow) and contacts the adulterant test strips. After sample has flowed pass the adulterant test strips, the sample contacts the analyte test strips (see, e.g., FIG. 14) The liquid flows in a controlled manner sequentially along the bottom of the test strips toward the assay device lid body vent hole. The liquid movement helps to push all trapped air in the channel the vent, which prevents formation of air bubbles in the channel that can prevent test strips from running correctly. Sample contacts a limited portion of the test strips and, accordingly, does not flood the test strips. As shown in FIG. 15, the regions of the test strips between the solid lines are contacted by the sample. The regions above the solid lines are not contacted directly by the sample; sample flows from the bottom of the test strips into the test strips by capillary action.

In some embodiments, the camera captures another image of the assay device lid and, optionally, verifies acceptability to proceed with the assay. In some embodiments, a light source (e.g., a plurality of LEDs) illuminates the lid to improve the quality of the image. In some embodiments, the image is analyzed to identify fiducial marks on the assay device lid label. The fiducial marks are small features printed on the lid near the test strip windows to provide reference points for subsequent processing steps to assure accurate image analysis. In some embodiments, the barcode has its own fiducial marks to allow the barcode to be identified and read even if the label is askew. If the barcode and fiducial marks can be located and properly read, then operation proceeds. Otherwise, the site administrator is alerted and decides whether to proceed or not.

In some embodiments, test strips take between two and eight minutes to develop. In some embodiments, the processor periodically captures additional images of the assay device lid during development of the test strips (e.g., up to approximately eight minutes). In some embodiments, the processor analyzes captured image data to determine test validity and test results. In some embodiments, if assay strip lines are visible after two minutes, the test is concluded and operation proceeds to the next steps. Otherwise, images are recorded and analyzed at subsequent intervals (e.g., approximately every minute until eight minutes have elapsed). If any of the drug or control lines do not become visible, the assaying device is sent to the lab for further analysis.

In some embodiments, the processor displays test validity and test results for a local user and/or administrator (e.g., on a display component). In some embodiments, the processor communicates test validity and test results to a remote host computer. In some embodiments, the user and/or administrator opens the reader apparatus lid and removes the assay device. In some embodiments, the user and/or administrator removes a reservoir to contain leaks to dispose of leaked sample and/or to clean the reservoir.

In some embodiments of using the technology provided herein, a test administrator at a local site will give a user, e.g., an employee applicant, a new unused assay device. The employee applicant will then deposit a fluid specimen into the cup. The lid will then be installed onto the cup. The assay device will then be placed in the receiver of the reader apparatus and a switch will be pressed to supply a start signal to a microprocessor-based controller. The controller will then initiate and execute a test procedure that involves initially reading a barcode on the lid. The controller will then actuate the laser source to produce a laser, pierce the lid label to release an airlock, and allow sample to flow from the cup to the test strips. The microprocessor-based controller will actuate a camera to cause it to generate an electronic representation of the visual indications provided by the respective test strips. The electronic representations generated by the camera are then processed by the image processor to interpret the characteristics of the fluid specimen. The resulting output data can then be displayed, stored, printed, and/or communicated to a remote site, e.g. via modem. Unless this test produces a negative result, the entire assaying device containing the uncontaminated specimen is then typically shipped to a remote laboratory for further analysis.

Analytes

The technology provided herein relates to assaying for the presence, absence, concentration, and/or amount of an analyte, e.g., a drug. In some embodiments, the technology assays for the presence, absence, concentration, and/or amount of one or more of amphetamine, barbiturate, benzodiazepine, buprenorphine, cocaine, tetrahydrocannabinol (THC), ethyl glucuronide, methadone, methamphetamine, 3,4-methylenedioxy-methamphetamine (MDMA), opiate, oxycodone, phencyclidine, propoxyphene, 6-monoacetyl morphine, morphine, fentanyl, tramadol, synthetic cannabinoids (e.g., K2, spice, etc.; see, e.g., Liu (2018) Am J Clin Pathol. 149(2): 105-116; Ford (2017) Trends Pharmacol Sci. 38(3): 257-276; Davidson (2017) Adv Pharmacol. 80: 135-168, each of which is incorporated herein by reference), and ketamine. In some embodiments, the technology provides a test device that indicates the presence, absence, concentration, and/or amount of any of the foregoing by measuring the presence, absence, concentration, and/or amount of a metabolite of any of the foregoing.

Samples

In some embodiments, the technology described herein is configured to assay a sample, including liquid samples as described herein. In some embodiments of the technology, the sample is a biological sample. Biological specimens include but are not limited to a sample from a subject such as an animal (e.g., a mammal (e.g., a primate (e.g., human))). A sample from a subject can be of any appropriate type, such as a sample of fluid (e.g., urine), tissue, organ, or a combination thereof. The biological specimen can also be a sample of other biological material, such as food, including food such as material derived from plants or animals or combinations thereof. In some embodiments, the sample is processed prior to introduction into the chamber. In some embodiments, the assay device includes reagents for use in such processing. In some embodiments, a sample and reagent are combined within the assay device. In some embodiments, a reagent is used to process a sample, e.g., to digest a solid sample with appropriate reagents (e.g., chemicals, acids, bases, and/or enzymes (e.g., proteases)). In some embodiments, reagents are used to extract an analyte from a sample. For example, in some embodiments, the technology relates to extracting an antigen from a biological entity (e.g., an etiological agent (e.g., bacteria, parasites, viruses, or prions such as known in the art)).

While a number of different biological samples are suitable for collection and assay by the present technology, commonly collected samples are biological samples, including but not limited to fluid samples (e.g., urine, blood, serum, saliva, semen, secretions (e.g., vaginal secretions), central nervous system fluids, lavages, and the like). However, the specimen can also be an environmental sample, such as a sample of soil, water, wastewater, landfill, or landfill leachate.

In some embodiments, the assay device accommodates sample volumes of between approximately 0.0001 milliliter to approximately 1,000 milliliters. In some embodiments, the sample is diluted or concentrated depending on the concentration of the analyte and the sensitivity of the test device. As a general guideline the sample may be greater than 1.0 milliliter, 0.1 milliliter, 0.01 milliliter, 0.001 milliliter, or approximately 0.0001 milliliter and may be less than approximately 1 milliliter, 5 milliliters, 10 milliliters, 50 milliliters, 100 milliliters, 250 milliliters, 500 milliliters, 750 milliliters, 1,000 milliliters, or approximately 2,000 milliliters. However, the present technology envisions additional ranges depending on the needs of the user.

Uses

The technology finds use in a variety of applications settings. In some embodiments, the assay device described herein finds use in forensic applications. In some embodiments, the assay device finds use by an employer (e.g., to monitor drug use by employees onsite and/or offsite). In some embodiments, the assay device finds use in criminal justice (e.g., to monitor drug use by individuals on probation, parole, under house arrest, in post-incarceration rehabilitation, etc.) In some embodiments, the assay device finds use in insurance (e.g., to monitor insureds and/or to evaluate risk). In some embodiments, the assay device finds use in rehabilitation of drug users or addicts. In some embodiments, the technology finds use in a home, medical clinic, emergency room, or doctor's office.

Kits

Some embodiments provide a kit comprising one or more assay device cups as described herein (e.g., comprising an assay device cup and an assay device lid as described herein). In some embodiments, the kit is provided for use with a reader apparatus as described herein.

Although the disclosure herein refers to certain illustrated embodiments, it is to be understood that these embodiments are presented by way of example and not by way of limitation.

EXAMPLE

An assay device comprising a plurality of test strips configured to detect the presence of drugs of abuse is provided to a person in need of a drug-of-abuse test. The person goes to the lavatory. In the lavatory, the person urinates into the cup, engages the lid to the cup, and gives the assay device to a test administrator. The test administrator inserts the assay device into a reader apparatus and initiates the assay. The reader apparatus actuates a laser source to produce a laser. The laser contacts a laser target on the label of the assay device lid and pierces the label. The assay device lid vent hole is opened, an airlock is released, and urine flows to contact the test strips and adulteration test strips. If present, one or more analytes in the sample produces an observable test result on a test strip that is viewed through the test strip viewing window. A series of images are recorded during the process and the reader apparatus analyzes the images to locate lines on the test strips to validate the test and to produce test results that are reported to the test administrator. The test administrator reports the results of the test and disposes of the used assay device in the appropriate biohazard container.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. An assay device for detecting an analyte in a liquid sample, said assay device comprising an assay device cup and an assay device lid, wherein:
   said assay device cup comprises an interior volume configured to hold a liquid sample; and
   said assay device lid comprises:
   a lid body inlet hole;
   an analyte test strip;
   a gasket comprising a gasket inlet hole aligned with said lid body inlet hole, wherein said gasket is fit into the assay device lid to retain the analyte test strip in the assay device lid and to separate the analyte test strip from the interior volume of the assay device cup when said assay device lid is engaged with said assay device cup;
   a vent hole configurable between an open state and a closed state; and
   a label comprising a laser-pierceable material,
   wherein the label covers the vent hole to provide the vent hole in the closed state thereby producing an airlock that prevents movement of the liquid sample through the gasket inlet hole and lid body inlet hole to the analyte test strip and piercing the label produces a hole in the label to provide the vent hole in the open state thereby releasing the airlock, thereby providing a metered amount of said liquid sample to said analyte test strip through the gasket inlet hole and lid body inlet hole.

2. The assay device of claim 1, wherein said assay device lid further comprises a second test strip configured to detect an adulterant in the liquid sample.

3. The assay device of claim 1 wherein said assay device lid comprises a shape that is complementary to an assay device receiver of a reader apparatus and said assay device lid compels insertion of the assay device into the reader apparatus in a particular orientation.

4. The assay device of claim 3 wherein said assay device lid has a D-shape.

5. The assay device of claim 1 wherein said assay device lid comprises the label comprising an adhesive tab configured to provide a tamper-evident seal for the assay device.

6. The assay device of claim 1 wherein said assay device lid comprises the label comprising a barcode.

7. The assay device of claim 1 wherein said assay device lid comprises a test strip viewing window providing imaging access to said analyte test strip.

8. The assay device of claim 1, wherein said gasket seals said sample in said assay device when said assay device lid is engaged with said assay device cup.

9. The assay device of claim 1 wherein said liquid sample is a biological sample.

10. The assay device of claim 1 wherein said liquid sample is urine.

11. The assay device of claim 1 wherein said analyte is a drug.

12. The assay device of claim 1 wherein said analyte is a drug of abuse.

* * * * *